United States Patent [19]

Levitt

[11] 4,452,627

[45] Jun. 5, 1984

[54] AGRICULTURAL UREAS AND ISOUREAS

[75] Inventor: George Levitt, Wilmington, Del.

[73] Assignee: E. I. Du Pont de Nemours and Company, Wilmington, Del.

[21] Appl. No.: 421,415

[22] Filed: Sep. 22, 1982

Related U.S. Application Data

[60] Division of Ser. No. 184,371, Sep. 15, 1980, Pat. No. 4,370,479, which is a continuation-in-part of Ser. No. 98,724, Nov. 30, 1979, abandoned.

[51] Int. Cl.³ .................................................. A01N 43/54
[52] U.S. Cl. ............................................................ 71/92
[58] Field of Search ............................................. 71/92

[56] References Cited

U.S. PATENT DOCUMENTS 4,169,719 10/1979 Levitt ..................................... 71/92

Primary Examiner—Catherine L. Mills

[57] ABSTRACT

Condensed ring aromatic ureas and isoureas are useful as plant growth regulants and as pre- and/or post-emergence herbicides.

14 Claims, No Drawings

AGRICULTURAL UREAS AND ISOUREAS

RELATED APPLICATION

This is a division of application Ser. No. 184,371, filed Sept. 15, 1980, which is a continuation-in-part of my copending application U.S. Ser. No. 098,724 filed Nov. 30, 1979, now abandoned.

BACKGROUND OF THE INVENTION

This invention relates to condensed ring aromatic ureas and isoureas which are useful as agricultural chemicals.

Netherlands Pat. No. 121,788, published on Sept. 15, 1966, discloses the preparation of compounds of Formula 1 and their use as general or selective herbicides:

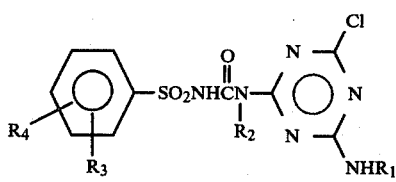
(1)

wherein
$R_1$ and $R_2$ may independently be alkyl of 1–4 carbon atoms; and
$R_3$ and $R_4$ may independently be hydrogen, chlorine or alkyl of 1–4 carbon atoms.

U.S. Pat. No. 4,127,405, issued to Levitt on Nov. 28, 1978, discloses compounds of Formula 2, their agriculturally suitable salts, and methods of using them as selective, as well as general, herbicides having both pre-emergence and post-emergence activity:

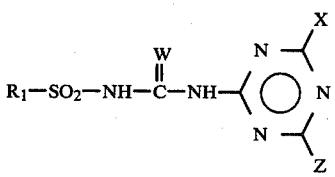
(2)

wherein
$R_1$ can be selected from several aromatic possibilities including

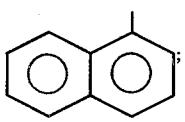

W is oxygen or sulfur;
X is hydrogen, chlorine, bromine, methyl, ethyl, alkoxy of 1–3 carbon atoms, trifluoromethyl, $CH_3S-$ or $CH_3OCH_2$; and
Z is methyl or methoxy.

U.S. Pat. No. 4,120,691, issued to Levitt on Oct. 17, 1978, discloses compounds of Formula 3, their agriculturally suitable salts, and methods of using them as general herbicides having both pre-emergence and post-emergence activity and as plant growth regulants:

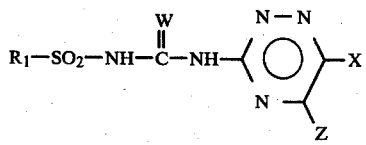
(3)

wherein
$R_1$ can be selected from several aromatic possibilities including

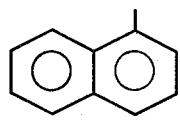

W is oxygen or sulfur; and
X and Z are independently hydrogen, methyl or methoxy.

U.S. Pat. No. 4,169,719, issued to Levitt on Oct. 2, 1979, discloses compounds of Formula 4, their agriculturally suitable salts, and methods of using them as selective, as well as general, herbicides having both pre-emergence and post-emergence activity:

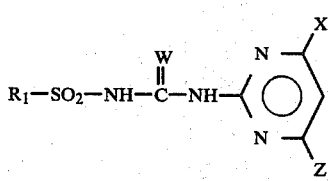
(4)

wherein
$R_1$ can be selected from several aromatic possibilities including

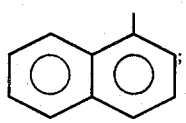

W is oxygen or sulfur;
X is hydrogen, chlorine, bromine, methyl, ethyl, alkoxy of 1–3 carbon atoms, trifluoromethyl, $CH_3S-$ or $CH_3OCH_2-$; and
Z is methyl or methoxy.

The presence of undesired vegetation causes substantial damage to useful crops, especially agricultural products which satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. Also, for man to conduct manufacturing, transportation, communications and other such activities, he must wage a constant battle to prevent encroachment of undesirable vegetation into areas where such activities are performed.

A wide variety of materials useful for killing or inhibiting (controlling) the growth of undesired vegetation is available; such materials are commonly referred to as herbicides. A need still exists, however, for more effective herbicides.

SUMMARY OF THE INVENTION

According to this invention, there is provided compounds of Formulas 5 and 6, which are useful as herbicides, and/or plant growth regulators. Some of the herbicides are useful for selective weed control in crops such as rice:

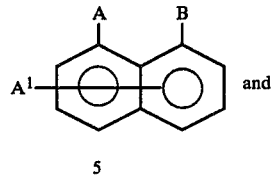

5

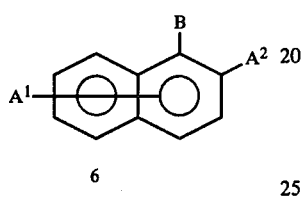

6 wherein $A^1$ is H, F, Cl, Br, $CH_3O$ or $NO_2$; A and $A^2$ are independently

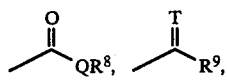

Cl, F, Br, $NO_2$, $-CH_3$, $-SO_2NR^1R^2$, $-SO_2N(CH_3)(OCH_3)$, $-S(O)_nR^3$, $-OR^3$, $-OSO_2R^3$ or $-OSO_2CF_3$;

B is

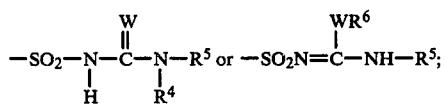

n is 0, 1 or 2;
Q is O, S or $NR^7$;
$R^1$ is $C_1$-$C_4$ alkyl;
$R^2$ is $C_1$-$C_4$ alkyl;
$R^3$ is $C_1$-$C_4$ alkyl;
$R^4$ is H or $CH_3$;

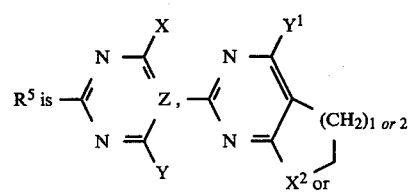

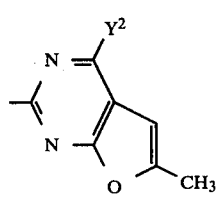

$R^6$ is $C_1$-$C_6$ alkyl;

$R^7$ is H, $-OCH_3$ or $C_1$-$C_4$ alkyl;
when Q is O or S then $R^8$ is $C_1$-$C_6$ alkyl, $C_3$-$C_6$ alkenyl, $CH_2CH_2OCH_3$, $CH_2CH_2OCH_2CH_3$, $C_5$-$C_6$ cycloalkyl, $C_4$-$C_7$ cycloalkylalkyl, phenyl, benzyl, or phenyl or benzyl substituted with one or two groups selected from $CH_3$, Cl or $OCH_3$; and when Q is O, $R^8$ may also be $CH_2CH_2Cl$; when Q is $NR^7$ then $R^8$ is H, $C_1$-$C_4$ alkyl, $C_3$-$C_4$ alkenyl and $R^8$ and $R^7$ taken together can be $-(CH_2)_4-$, $-(CH_2)_5-$ or $-CH_2CH_2OCH_2CH_2-$ and with the proviso that when $R^7$ is $CH_3O$, $R^8$ is $CH_3$;
$R^9$ is $C_1$-$C_6$ alkyl, $C_3$-$C_6$ alkenyl, $C_5$-$C_6$ cycloalkyl, $C_4$-$C_7$ cycloalkylalkyl, benzyl, or benzyl substituted with one or two groups selected from $CH_3$, Cl or $OCH_3$;
$R^{10}$ is H or $CH_3$;
$R^{11}$ is $C_1$-$C_3$ alkyl;
$R^{12}$ is $C_1$-$C_4$ alkyl or $C_3$-$C_6$ alkenyl;
T is O or $N-OR^{12}$;
W is O or S;
X is $CH_3$, $CH_3O$ or $CH_3CH_2O$;
$X^2$ is O or $CH_2$;
Y is H, $C_1$-$C_3$ alkyl, $CH_3OCH_2$, $CH_3CH_2OCH_2$, $OCH_2CO_2-$(H or $C_1$-$C_2$ alkyl), $OCH(CH_3)CO_2$(H or $C_1$-$C_2$ alkyl), O$-$($C_1$-$C_3$ alkyl), O$-$($C_3$-$C_4$ alkenyl) or $NR^{10}R^{11}$;
$Y^1$ is H, $CH_3$ or $OCH_3$;
$Y^2$ is H or $CH_3$; and
Z is N, CH or $CCH_3$;

and their agriculturally suitable salts.

Preferred for reasons of higher activity and/or lower cost and/or greater ease of synthesis are:

(1) Compounds of formula 5 in which

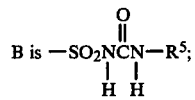

(2) Compounds of formula 6 in which

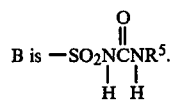

More preferred in increasing order and for reasons of even higher activity and/or lower cost and/or greater ease of synthesis are:

(3) Compounds of preferred 1 in which A is Cl, $NO_2$, $CH_3$, $CH_3O$, $CH_3SO_2O$, $CH_3SO_2$, $SO_2N(CH_3)_2$, $SO_2N(CH_3)(OCH_3)$, $CH_3S$ or $CH_3SO$;

(4) Compounds of preferred 3 in which $A^1$ is H;

(5) Compounds of preferred 4 in which Y is $CH_3$ or $CH_3O$; $X^2$ is O, and $Y^2$ is $CH_3$;

(6) Compounds of preferred 5 in which A is Cl;

(7) Compounds of preferred 2 in which $A^2$ is Cl, $NO_2$, $CH_3$, $CH_3O$, $CH_3SO_2O$, $CH_3SO_2$, $SO_2N(CH_3)_2$, $SO_2N(CH_3)(OCH_3)$, $CH_3S$ or $CH_3SO$;

(8) Compounds of preferred 7 in which $A^1$ is H;

(9) Compounds of preferred 8 in which $X^2$ is O, Y is $CH_3$ or $CH_3O$ and $Y^2$ is $CH_3$;

(10) Compounds of preferred 9 in which $A^2$ is Cl.

It is noted that compounds of preferred 10 demonstrate selective weed control in rice.

Specifically preferred for reasons of highest activity and/or lowest cost and/or greatest ease of synthesis are:

2-chloro-N-[(4,6-dimethylpyrimidin-2-yl)aminocarbonyl]-1-naphthalenesulfonamide;
2-chloro-N-[(4,6-dimethoxypyrimidin-2-yl)aminocarbonyl]-1-naphthalenesulfonamide;
2-chloro-N-[(4-methoxy-6-methylpyrimidin-2-yl)aminocarbonyl]-1-naphthalenesulfonamide;
2-chloro-N-[(4,6-dimethyl-1,3,5-triazin-2-yl)aminocarbonyl]-1-naphthalenesulfonamide;
2-chloro-N-[(4,6-dimethoxy-1,3,5-triazin-2-yl)aminocarbonyl]-1-naphthalenesulfonamide;
2-chloro-N-[(4-methoxy-6-methyl-1,3,5-triazin-2-yl)aminocarbonyl]-1-naphthalenesulfonamide;
2-chloro-N-[(5,6-dihydro-4-methylfuro[2,3-d]pyrimidin-2-yl)aminocarbonyl]-1-naphthalenesulfonamide;
2-chloro-N-[(5,6-dihydro-4-methoxyfuro[2,3-d]pyrimidin-2-yl)aminocarbonyl]-1-naphthalenesulfonamide;
2-chloro-N-[(4,6-dimethylfuro[2,3-d]pyrimidin-2-yl)aminocarbonyl]-1-naphthalenesulfonamide;
8-chloro-N-[(4,6-dimethylpyrimidin-2-yl)aminocarbonyl]-1-naphthalenesulfonamide;
8-chloro-N-[(4,6-dimethoxypyrimidin-2-yl)aminocarbonyl]-1-naphthalenesulfonamide;
8-chloro-N-[(4-methoxy-6-methylpyrimidin-2-yl)aminocarbonyl]-1-naphthalenesulfonamide;
8-chloro-N-[(4,6-dimethyl-1,3,5-triazin-2-yl)aminocarbonyl]-1-naphthalenesulfonamide;
8-chloro-N-[(4,6-dimethoxy-1,3,5-triazin-2-yl)aminocarbonyl]-1-naphthalenesulfonamide;
8-chloro-N-[(4-methoxy-6-methyl-1,3,5-triazin-2-yl)aminocarbonyl]-1-naphthalenesulfonamide;
8-chloro-N-[(5,6-dihydro-4-methylfuro[2,3-d]pyrimidin-2-yl)aminocarbonyl]-1-naphthalenesulfonamide;
8-chloro-N-[(5,6-dihydro-4-methoxyfuro[2,3-d]pyrimidin-2-yl)aminocarbonyl]-1-naphthalenesulfonamide; and
8-chloro-N-[(4,6-dimethylfuro[2,3-d]pyrimidin-2-yl)aminocarbonyl]-1-naphthalenesulfonamide.

The following novel compounds of Formulas 7, 8, 43 and 44, are useful as intermediates:

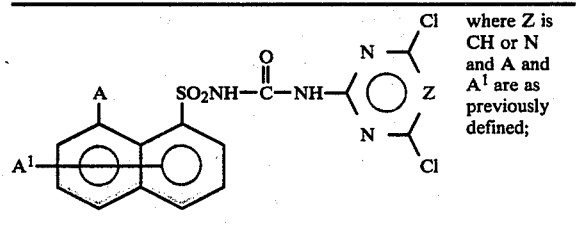

where Z is CH or N and A and $A^1$ are as previously defined;

43

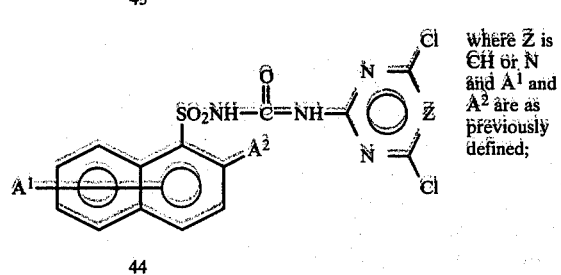

where Z is CH or N and $A^1$ and $A^2$ are as previously defined;

44

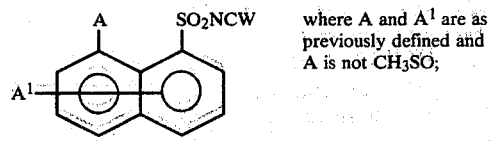

where A and $A^1$ are as previously defined and A is not $CH_3SO$;

8

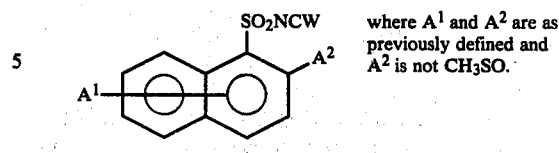

where $A^1$ and $A^2$ are as previously defined and $A^2$ is not $CH_3SO$.

7

Specifically preferred intermediates are: 8-chloronaphthalenesulfonyl isocyanate; and 2-chloronaphthalenesulfonyl isocyanate.

Synthesis

Many of the compounds of 5 and 6 are prepared as shown in Equation 1 by the reaction of an appropriately substituted naphthalene sulfonylisocyanate or isothiocyanate with an appropriate aminopyrimidine or aminotriazine.

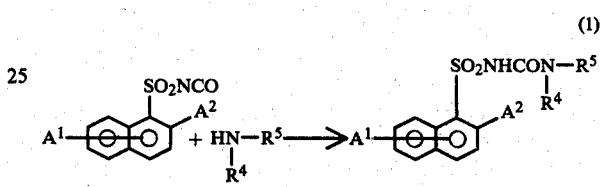

(1)

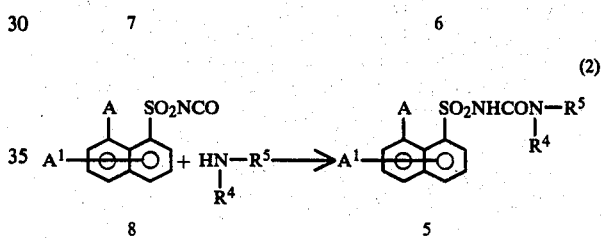

(2)

The addition of the sulfonylisocyanate and the heterocyclic amine can be effected in methylene chloride, dry acetonitrile or dry tetrahydrofuran by heating under reflux protected from moisture. The products can be isolated by evaporation of the solvent under reduced pressure and cautious elutriation of the residue. Chromatography (silica gel or florisil) may also be required.

The preparation of the substituted sulfonylisocyanates 7 and 8 can be broadly envisioned from the corresponding sulfonamide.

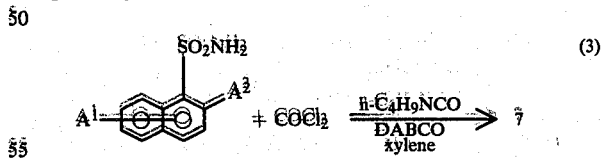

(3)

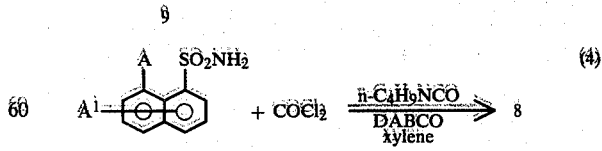

(4)

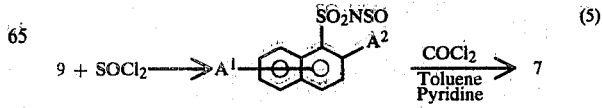

(5)

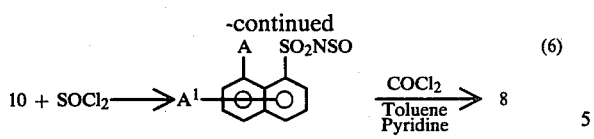

The reaction of 9 or 10 as in (3) or (4) may be effected by heating with an alkyl isocyanate, e.g., butyl isocyanate and a catalytic amount of 1,4-diazobicyclo[2,2,-2]octane (DABCO) in xylene or some other inert solvent of sufficiently high boiling point, e.g., >135°, to approximately 130°–160° C. Phosgene is added to the mixture until an excess of phosgene is present as indicated by depression of the boiling point.

After the mixture is cooled, the product solution may be separated by decantation or filtration to remove small amounts of insoluble by-product, and the solvent and alkyl isocyanate may be distilled under reduced pressure. The crude sulfonylisocyanate may be used without further purification.

When 9 or 10 contains a base labile $A^2$ or A, the preparation of the sulfonamide and its subsequent phosgenation as described by H. Ulrich, B. Tucker and A. A. R. Sayigh, *J. Org. Chem.*, 34, 3200 (1969), may be used to prepare 7 or 8 respectively.

The required sulfonamides 9 or 10 may be prepared by several procedures. Most generally, the sulfonamides may be prepared from the sulfonyl chlorides 11 and 12 as described in "Preparative Organic Chemistry", ed. G. Hilgetag and A. Martini, J. Wiley and Sons, New York (1972). The sulfonyl chlorides may be prepared by chlorination of the sulfonic acids 13 and 14, by methods described by Hilgetag and Martini, op. cit. The preparation of these acids is described in the art. These compounds may be further transformed by methods known in the art to yield other disclosed sulfonic acids.

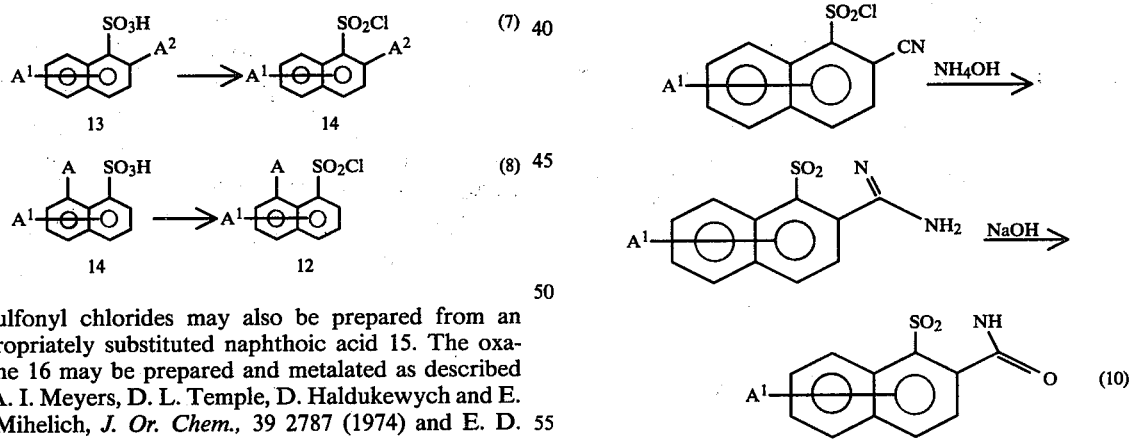

Sulfonyl chlorides may also be prepared from an appropriately substituted naphthoic acid 15. The oxazoline 16 may be prepared and metalated as described by A. I. Meyers, D. L. Temple, D. Haldukewych and E. D. Mihelich, *J. Or. Chem.*, 39 2787 (1974) and E. D. Mihelich and A. I. Meyers, *J. Org. Chem.*, 40 3158 (1975). Trapping of the anion with a disulfide can be effected following the procedure of H. W. Gschwend and A. Hamdan, *J. Org. Chem.*, 40 2008 (1975) to yield 17.

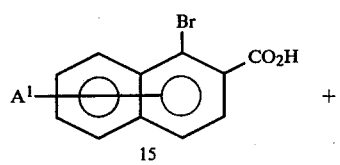

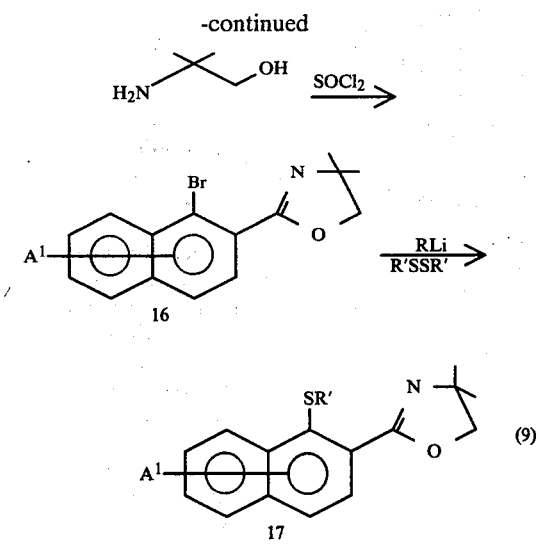

Oxidation of this thio ether to the sulfonyl chloride with concommitant deprotection of the acid may be effected after R. F. Langler, Z. A. Marini and E. S. Spalding, *Can. J. Chem.* 57, 3193 (1979).

Appropriately functionalyzed naphthalene sulfonimides 18 may also serve as precursors to 9. The required intermediates may be prepared according to H. P. Kaufmann and H. Zobel, *Ber.*, (1922); 1499, as shown in Equation (10).

Opening of the naphthalene sulfonimide by acid catalyzed alcoholysis may be effected, to yield 9. $A^2$ may be further transformed as will be described later to other functional groups used in this invention.

Naphthalene sulfonimides 18 may also be prepared by oxidation of the corresponding naphthalene isothiazole 19 after the work of G. Steiner, *J. Liebigs Ann.*, (1978) [4] 635. The naphthalene isothiazoles may be prepared from a suitably functionalized 2-naphthaldehyde by the method of H. Hagen and H. Flieg, Fed. Rep. Germany Pat. 2503699 (May 8, 1976).

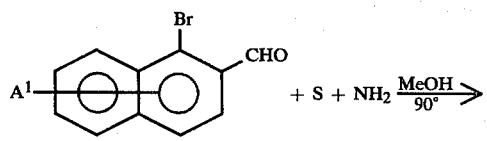

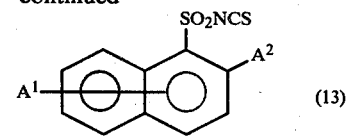  (13)

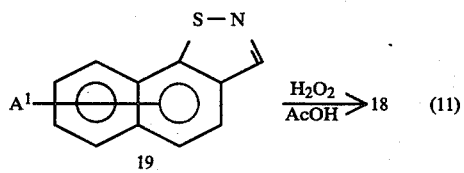  (11)

10 + CS$_2$ + KOH $\xrightarrow{\text{DMF}}$

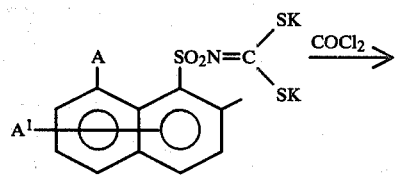

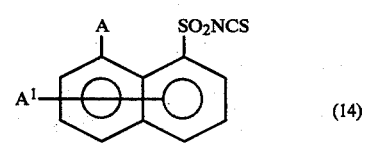  (14)

Naphthalene sulfonamide 10 may be prepared after the work of J. G. Lombardino, *J. Org. Chem.*, 36 1843, (1971), where A can be an electrophilic group and A$^1$ is not an electrofuge in the 7-position. A substituted naphthalene sulfonyl chloride is allowed to react with an amine. The resulting sulfonamide 20 may be metalated and trapped with an electrophile. The amide protecting group can be removed by methods known in the art.

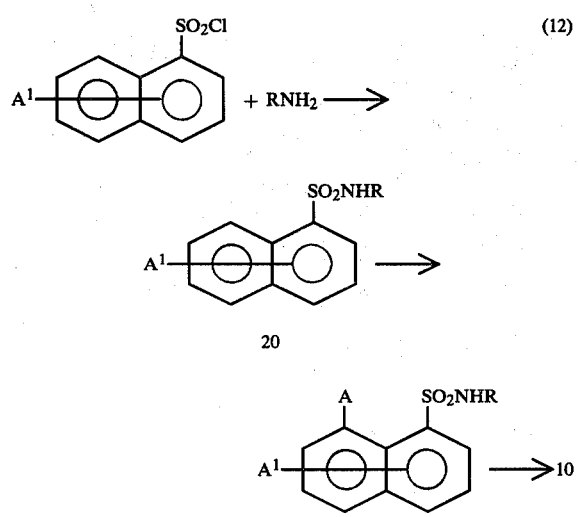

Where X=sulfur in 5 and 6, the useful sulfonyl isothiocyanate intermediates 22 and 24 may be prepared by reaction of the sulfonamide 9 or 10 with carbon disulfide when A or A$^2$ is not base labile as shown in (13) and (14).

The substituted sulfonamide is dissolved in dimethylformamide (DMF) with an equivalent amount of carbon disulfide. Two equivalents of potassium hydroxide are added portionwise at room temperature. The resulting mixture is stirred for 1–8 hours and diluted with ethyl acetate, diethyl ether or a similar aprotic solvent to cause the dipotassium salt of the dithiocarbamic acid to precipitate. The salt may be isolated, dried and suspended in an inert solvent such as xylene, benzene, carbon tetrachloride or methylene chloride. Phosgene is added to the stirred suspension at a temperature of about −20° to 25° C. and the mixture stirred for 1–3 hours.

The sulfonylisothiocyanate which is formed is usually soluble in the solvent and is isolated by filtering off the inorganic potassium chloride and concentrating the filtrate. These isothiocyanates may be unstable and tend to dimerize readily, however, the dimers can be used in the same manner as the parent isothiocyanates for the purpose of the invention.

As shown in (15) and (16), when W=sulfur, 5 and 6 may be prepared by reacting 22 or 24 with a substituted heterocyclic amine.

22 + HNR$_4$R$_5$ → 6    (15)

24 + HNR$_4$R$_5$ → 5    (16)

The reactions of (15) and (16) may be carried out in the manner described for (1) and (2).

Many compounds of 6 or 5 where W=sulfur may also be prepared by the reaction of appropriately substituted 9 or 10 with a heterocyclic isothiocyanate, SCNR$_5$.

9 + SCNR$_5$ → 6    (17)

10 + SCNR$_5$ → 5    (18)

These reactions may best be carried out by dissolving or suspending the sulfonamide and isothiocyanate in a 9 + CS$_2$ + KOH $\xrightarrow{\text{DMF}}$

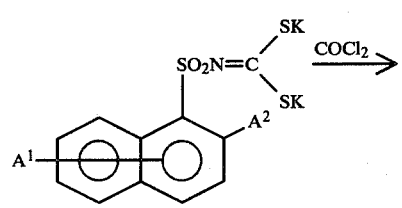

polar solvent such as acetone, acetonitrile, ethyl acetate or methylethyl ketone, adding an equivalent of a base such as potassium carbonate, and stirring the mixture at a temperature from ambient up to reflux for one to twenty four hours. In some cases, the product precipitates from the reaction mixture and can be removed by filtration. The product is stirred in dilute mineral acid, filtered, and washed with cold water. If the product does not precipitate from the reaction mixture, it can be isolated by evaporation of the solvent, elutriation of the residue with dilute mineral acid, and filtering to obtain the insoluble product.

The heterocyclic isothiocyanates which are used may be prepared for example, according to the method of Japan Patent Application Publication: Kokai 51-143686, June 5, 1976, or that of W. Abraham and A. Barnikow, *Tetrahedron* 29, 691–7 (1973). When B=

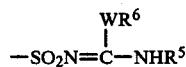

and W=oxygen, 6 and 5 may be prepared as shown in (19) and (20).

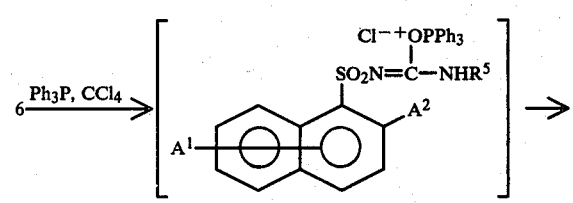

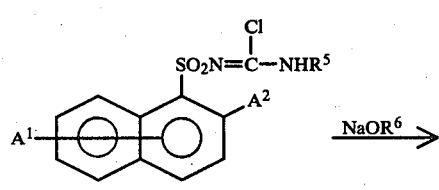

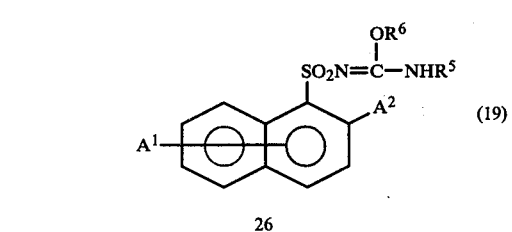

(19)

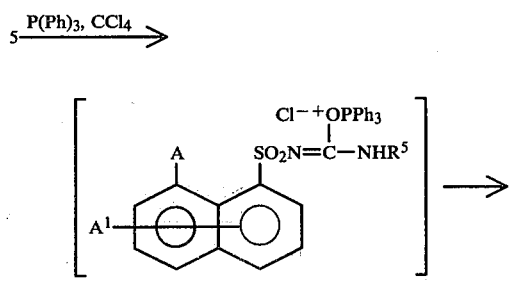

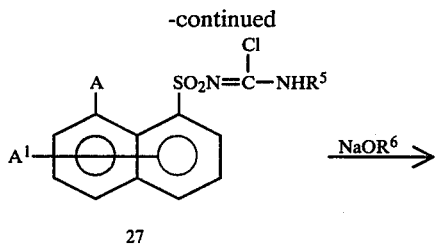

27

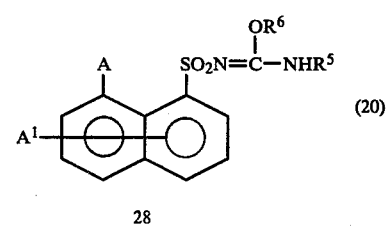

(20)

28

An equivalent or excess amount of carbon tetrachloride is added to a solution of 5 or 6 and triphenyl phosphine in an inert aprotic solvent such as acetonitrile at about −10° to 25° C. The resulting reaction is completed by stirring at the designated temperature for 10 to 48 hours to obtain a carbamimidoyl halide 25 or 27, which may be isolated by passing the reaction solution through a silica gel column to remove the triphenyl phosphine oxide and then removing the solvent by evaporation under reduced pressure.

25 or 27 may be converted directly to 26 or 28 by reacting the reaction mixture with a metal alkoxide at −10° to 25° C. The reaction is completed by stirring at ambient temperature for 2 to 24 hours. The crude products 28 or 26 are isolated by filtering off precipitated metal halide and removing the solvent by evaporation under reduced pressure. Further purification may be accomplished by recrystallization or column chromatography on silica gel.

When W=oxygen and B=

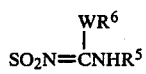

and A or $A^2$ is not a base labile functional group, particularly when $R^5$ is pyrimidinyl; 26 and 28 may be prepared as described in (21) and (22).

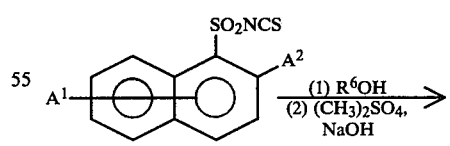

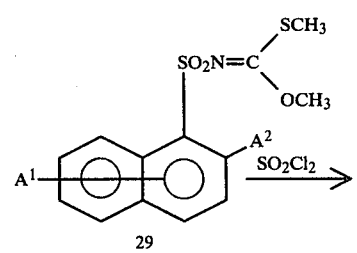

29

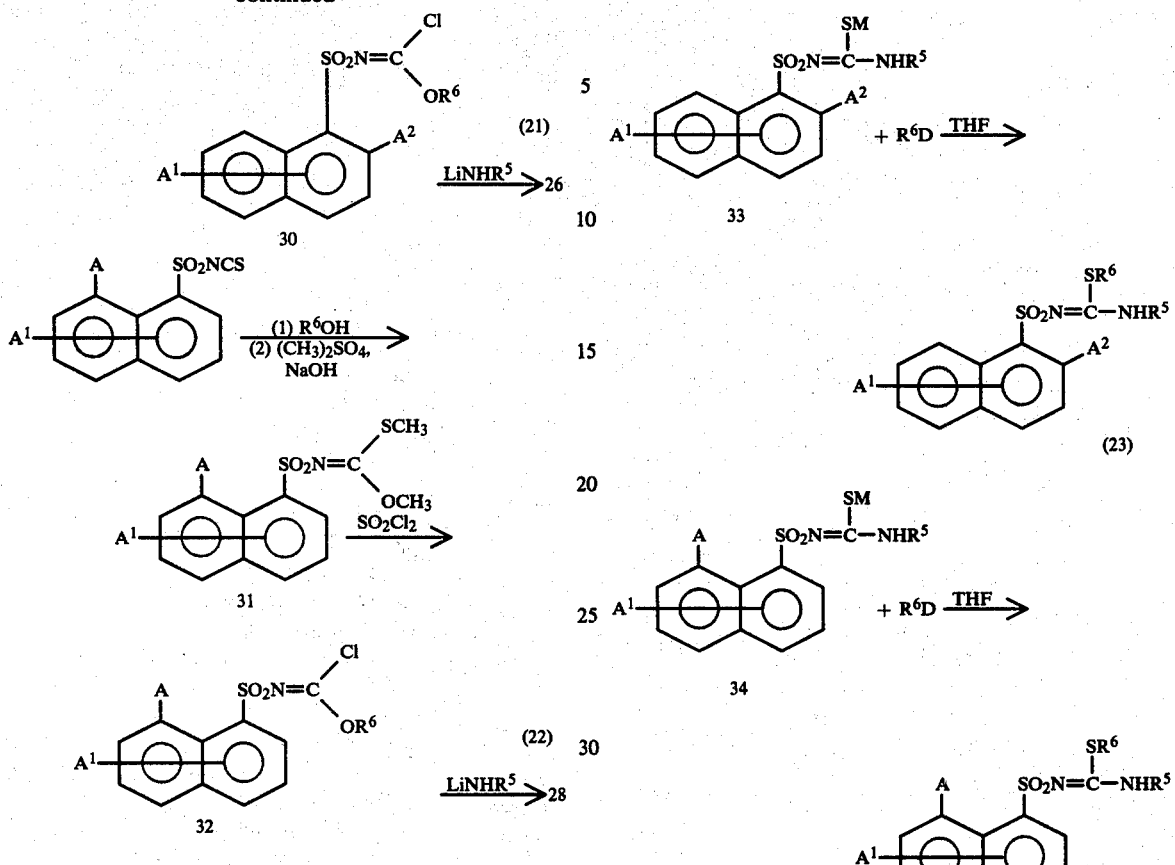

29 and 31 are known in the art, R. Gompper and W. Hagele, *Chem. Ber.*, 99, 7885 (1966). 30 and 32 may be prepared by allowing 29 and 31 to react with sulfuryl chloride in an inert organic solvent such as methylene chloride or chloroform at a temperature between −10° to 30° C. 30 and 32 may be isolated by evaporation of the solvent.

The lithium salt of the corresponding 2-aminoheterocyclic compound can be prepared by reacting the aminoheterocyclic compound with n-butyl lithium in a solvent such as tetrahydrofuran. To this salt solution is added a solution of 30 or 32 in tetrahydrofuran at a temperature of about −10° to 10° C. The reaction mixture is then stirred at 0°–10° C. for about 1–2 hours and at ambient temperature for about 1–4 hours. The products of 26 and 28 are isolated by filtering off the inorganic salts and removing the solvent under reduced pressure. The product may be further purified by recrystallization or by column chromatography on silical gel.

When W=sulfur and B=

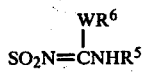

and A or $A^2$ is not base labile, 6 and 5 may be prepared by reacting the salt 33 or 34 with an alkylating agent $R^6D$ where D is a sulfate, chloride, bromide, or iodide and M is alkali metal, as shown in (23) and (24).

A solution of 5 or 6, W=sulfur is allowed to react with a strong base such as methyl lithium in dry tetrahydrofuran or other suitable solvent protected from moisture at −20°–60° C. The resulting anionic species may be trapped with the addition of a alkylating reagent $R^6D$. The product is isolated by evaporation of the solvent and recrystallization of the resulting residue from a solvent such as acetonitrile or ethyl alcohol.

When Q is $NR^7$, 36 may be prepared from those compounds where $A^2=$

Q=oxygen and $R^3$=methyl by reaction with dialkyl aluminum-N-alkylamide derivatives as shown in (25).

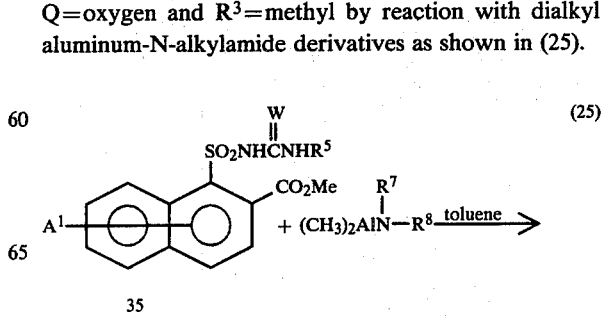

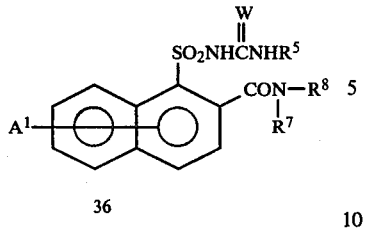

36

The intermediate alkylaminoaluminum compounds, prepared according to the teaching of A. Busha, M. Lipton and S. W. Weinreb, *Tetrahedron Letters* 4171 (1977), are co-mingled with a suspension of the esters in toluene, or similar inert solvent and the mixture is refluxed for one to six hours. The product may be isolated by evaporating the solvent, adding methylene chloride and aqueous hydrochloric acid to decompose the residual reaction mass and extracting the desired product into methylene chloride. Evaporation of the separated methylene chloride yields the desired product which can be purified by recrystallization from an inert solvent or by chromatography on silica gel.

When Q=sulfur, 37 may be prepared via the analogous reaction of 35 with the appropriate dialkylaluminum alkylthiolate as shown in (26)

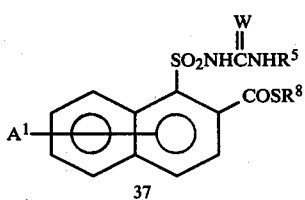

37

The aluminum thiolate used in these reactions can be prepared according to the method of R. P. Hatch and S. W. Weinreb, *Journal of Organic Chemistry*, 42, 3960 (1977). The reaction of the thiolate is best carried out in a neutral solvent such as toluene or xylene at reflux for one to three hours. Best results may be obtained when the aluminum thiolate compound is present in excess of the stoichiometric amount required. The compounds may be isolated as described for 36.

When $A^2=$

and W=oxygen, and $A^1$=H or $CH_3O$, 39 may be prepared by the directed ortho lithiation of 6 where $A^2$=Cl or Br and trapping of the anionic species with an acylating agent as shown in (27).

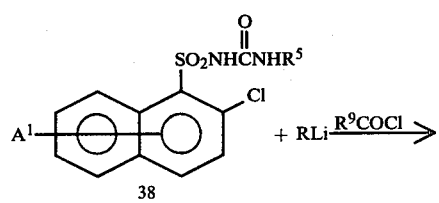

38

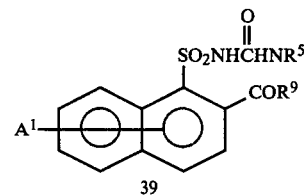

39

A solution of 38 in tetrahydrofuran or any suitable ethereal solvent may be allowed to react with excess alkyl lithium at temperatures of −40° to 50° C. The resulting polyanionic species may be captured by the acylating agent. Quenching of the product with saturated ammonium chloride may yield only the desired 39 as a stable reaction product.

The synthesis of a wide variety of organolithium compounds by many different procedures is known in the art. A summary of methods with bibliography is contained in *Organo-Metallic Compounds*, G. E. Coates, John Wiley and Sons, 1960, p. 3–21.

When $T=N—OR^3$, 6 may be prepared by standard oximation methods as outlined in *Preparative Organic Chemistry*, G. Hilgetag and A. Martini, Ed., John Wiley and Sons, p. 513.

The synthesis of heterocyclic amines has been reviewed in "The Chemistry of Heterocyclic Compounds", published by Interscience Publ., New York and London. 2-aminopyrimidines are described by D. J. Brown in Vol. XVI of this series. The 2-amino-1,3-5-triazine are reviewed by K. R. Huffman and in "The Triazines" of this same series. The synthesis of triazines is also described by F. C. Schaefer, U.S. Pat. No. 3,154,547 and by K. R. Huffmann and F. C. Schaeffer, *J. Org. Chem.* 28, 1816 (1963).

Braker, Sheehan, Spitzmiller and Lott, *J. Am. Chem. Soc.* 69, 3072 (1947) describe the preparation of 6,7-dihydro-4-methoxy-5H-cyclopentapyrimidin-2-amine by the following sequence of reactions.

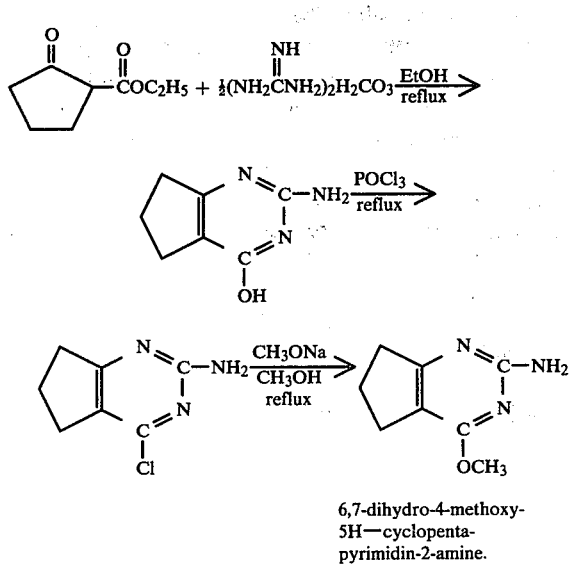

6,7-dihydro-4-methoxy-
5H—cyclopenta-
pyrimidin-2-amine.

An analogous sequence of reactions can be used to prepare 5,6,7,8-tetrahydro-4-methoxy-2-quinazolinamine.

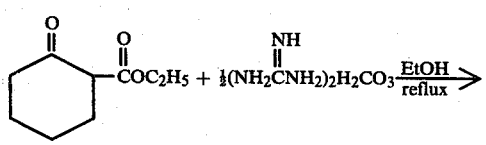

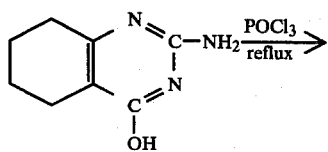

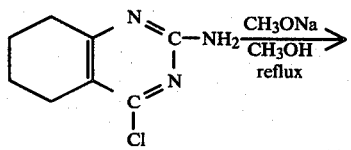

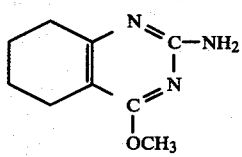

5,6,7,8-tetrahydro-4-methoxy-2-quinazolinamine.

Mitter and Bhattacharya, *Quart. J. Indian Chem. Soc.* 4, 152 (1927) describe the preparation of 5,6,7,8-tetrahydro-4-methyl-2-quinazolinamine as follows:

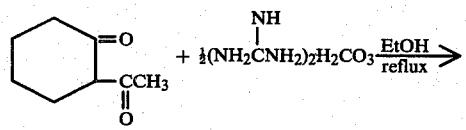

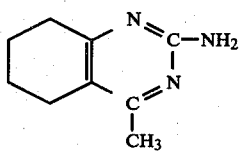

5,6,7,8-tetrahydro-4-methyl-2-quinazolinamine.

An analogous sequence of reactions can be used to prepare 6,7-dihydro-4-methyl-5H-pyrano[2,3-d]pyrimidin-2-amine starting with 2-acetyl-δ valerolactone [Korte and Wusten, *Tetrahedron* 19, 1423 (1963)].

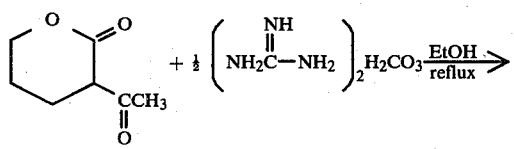

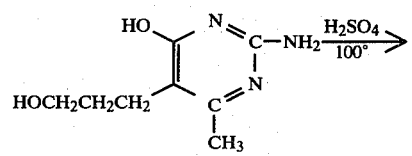

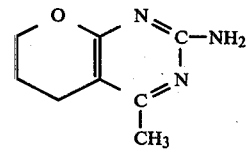

6,7-Dihydro-4-hydroxy-5H-pyrano[2,3-d]pyrimidin-2-amine can be prepared from diethyl 3-chloropropylmalonate, guanidine carbonate and sodium ethoxide in ethanol. Treatment of the product

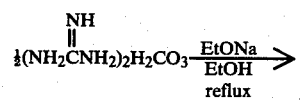

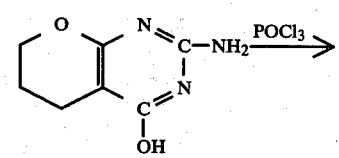

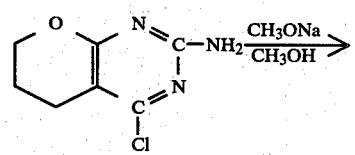

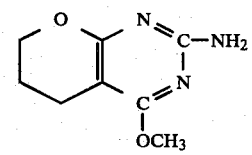

with phosphorus oxychloride gives 4-chloro-6,7-dihydro-5H-pyrano[2,3-d]pyrimidin-2-amine and subsequent reaction with sodium methoxide in refluxing methanol affords 6,7-dihydro-4-methoxy-5H-pyrano[2,3-d]pyrimidin-2-amine.

Compounds of $R^5$ where $Y^1$ is ethoxy can be prepared by a procedure analogous to the methoxy derivatives.

The furo[2,3-d]pyrimidine intermediates 42 where $Y^2$ is $CH_3$ have been reported in the literature of E. Bisagni et al., *Bull. Soc. Chim. Fr.*, (1969) 803. An apparently more efficient procedure is depicted in (28).

(28)

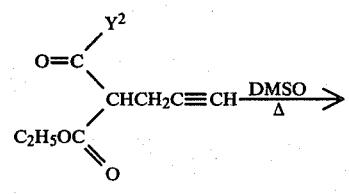

40

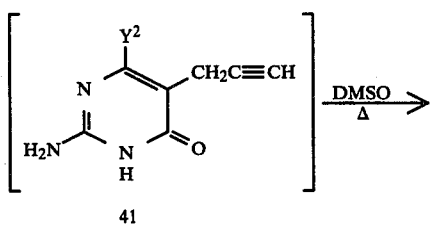

41

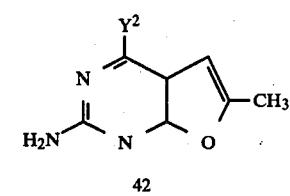

42

The keto-ester precursors 40 are prepared by well-known literature methods, e.g., J. F. Tinker and T. E. Whatmough, J. Amer. Chem. Soc. 74 5235 (1952).

Treatment of 40 with an excess of guanidine carbonate in a polar aprotic solvent such as dimethylsulfoxide (DMSO), at elevated temperatures, ambient pressure and preferably under an inert atmosphere, yields both 42 and 41 as products; the products are isolated upon dilution of the reaction mixture with acetone and water successively. The relative amounts of 42 and 41 isolated may be adjusted by varying the reaction time and/or temperature. Higher reaction temperatures and longer reaction times (e.g., 140° for 6 hours) favor the production of the furopyrimidine 42 over the uncyclized pyrimidine 41.

Agriculturally suitable salts of compounds of formulae 5 and 6 will also be useful herbicides and can be prepared by methods well-known in the art.

Starting materials and intermediates used to prepare compounds of this invention but not otherwise described herein, are disclosed in U.S. Pat. 4,127,405 and prior patent application U.S. Serial No. 910,965, now abandoned.

The invention is further illustrated by the following examples in which all temperatures are in degrees centigrade and all percentages are by weight unless otherwise specified.

EXAMPLE 1

Methyl 1-[(4,6-dimethoxypyrimidin-2-yl)aminocarbonyl]-aminosulfonyl-2- naphthalenecarboxylate A mixture containing 1.6 g of 2-amino-4,6-dimethoxypyrimidine, 30 ml of anhydrous methylene chloride and of 2-carbomethoxynaphthalenesulfonyl-isocyanate can be stirred at ambient temperature and pressure for 16 hours. It can then be filtered to remove unreacted amine and the filtrate evaporated at a temperature up to 40° and at reduced pressure. The resulting residue may be elutriated with chlorobutane or a chlorobutane-methylene chloride and the solid product named above separated by filtration and dried.

EXAMPLE 2

2-chloro-N-[(4,6-dimethoxypyrimidin-2-yl)aminocarbonyl]-1-naphthalenesulfonamide To 3 ml of a methylene chloride solution of 0.59 g (0.0042 mol) of 2-amino-4,6-dimethoxypyrimidine in a magnetically stirred 50 ml round bottom flask protected from moisture was added 2 ml of a methylene chloride solution containing 1 g (0.004 mol) of 2-chloro-1-naphthalenesulfonylisocyanate. The reaction mixture was allowed to stir at room temperature for 18 hours. The solvent was removed in vacuo to yield the crude product. The product was purified by elutriation with chlorobutane as previously described to yield a pale yellow solid, m.p. 165°–168°.

The following compounds were similarly prepared:
2-chloro-N-[(4,6-dimethylpyrimidin-2-yl)aminocarbonyl]-1-naphthalenesulfonamide, m.p. 210°;
2-chloro-N-[(4-methoxy-6-methylpyrimidin-2-yl) aminocarbonyl]-1-naphthalenesulfonamide, m.p. 115°;
2-chloro-N-[(4,6-dimethyl-1,3,5-triazin-2-yl)aminocarbonyl)-1-naphthalenesulfonamide, m.p. 95°–100°;
2-chloro-N-[(4,6-dimethoxy-1,3,5-triazin-2-yl)aminocarbonyl]-1-naphthalenesulfonamide, m.p. 125°; and
2-chloro-N-[(4-methoxy-6-methyl-1,3,5-triazin-2-yl)-aminocarbonyl]-1-naphthalenesulfonamide, m.p. 78°–80°.

EXAMPLE 3

Methyl 1-[[(4,6-dimethoxypyrimidin-2-yl amino) (methylthio)methylene]aminosulfonyl]-2-naphthalenecarboxylate To a suspension of methyl 1-[[(4,6-dimethoxypyrimidin-2-yl)aminothiocarbonyl]aminosulfonyl]-2-naphthalenecarboxylate in 200 ml of anhydrous tetrahydrofuran can be added 16.7 ml of 3M NaOCH3/MeOH solution. The resulting reaction mixture can be heated to reflux, 3.1 ml of methyl iodide in 10 ml of anhydrous tetrahydrofuran can be added; and the reaction mixture can be refluxed for 3 hours. The reaction mixture can be cooled to cause the formation of a precipitate which can be filtered off and washed with tetrahydrofuran to afford the desired product.

EXAMPLE 4

N,N-dimethyl-1-[[(4,6-dimethoxypyrimidin-2-yl)aminocarbonyl]aminosulfonyl]-2-naphthalenecarboxamide To 0.01 mole of the compound of Example 1 in 75 ml of toluene can be added 37 ml of a methylene chloride and toluene solution (3:5) containing 1.25 g of dimethylaluminum dimethylamide with stirring at ambient temperature. The resulting mixture can be heated to reflux for 2 hours, cooled, then 10 ml of methanol can be added and the solvents evaporated in vacuo. The resulting residue can be treated with a mixture of methanol, water, and dilute hydrochloric acid and the precipitated product filtered off to yield the desired product. Extraction of the aqueous filtrate with methylene chloride will give more product.

EXAMPLE 5

8-nitro-N-[(4-methoxy-6-methylpyrimidin-2-yl)aminocarbonyl]-1-naphthalenesulfonamide To 0.55 g (0.004 mol) of 2-amino-4-methoxy-6-methylpyrimidine dissolved in 5 ml of dry methylene chloride in a magnetically stirred 50 ml round bottom flask equipped with reflux condenser protected from moisture was added 4 ml of a methylene chloride solution of 1.0 g (0.004 mol) of 8-nitro-1-naphthalenesulfonylisocyanate. The reaction mixture was stirred with heating under reflux for ~16 hours. The cooled reaction mixture was concentrated in vacuo. The crude product was isolated by elutriation with chlorobutane in the usual manner to yield an off white solid, m.p. 145°–154°.

The following compounds were similarly prepared:
8-nitro-N-[(4,6-dimethylpyrimidin-2-yl)aminocarbonyl]-1-naphthalenesulfonamide, m.p. 178°–183°;
8-nitro-N-[(4,6-dimethoxypyrimidin-2-yl)aminocarbonyl]-1-naphthalenesulfonamide, m.p. 158°–160°;
8-nitro-N-[(4,6-dimethyl-1,3,5-triazin-2-yl)aminocarbonyl]-1-naphthalenesulfonamide, m.p. 95°–100°;
8-nitro-N-[(4-methoxy-6-methyl-1,3,5-triazin-2-yl)aminocarbonyl]-1-naphthalenesulfonamide, m.p. 152°–158°; and
8-nitro-N-[(4,6-dimethoxy-1,3-5-triazin-2-yl)aminocarbonyl]-1-naphthalenesulfonamide, m.p. 164°–170°.

Following the methods of the above examples and the general procedures described, the compounds in the following tables can be prepared by using the appropriate heterocyclic and aromatic moiety. These tables also illustrate the scope of this invention.

TABLE I

| $A^2$ | $A^1$ | $R^4$ | W | X | Y | Z |
|---|---|---|---|---|---|---|
| Cl | H | H | O | $CH_3$ | $CH_3$ | CH |
| Cl | H | H | O | $CH_3O$ | $CH_3$ | CH |
| Cl | H | H | O | $CH_3O$ | $CH_3O$ | CH |
| Cl | H | H | O | $CH_3$ | $CH_3$ | N |
| Cl | H | H | O | $CH_3$ | $CH_3O$ | N |
| Cl | H | H | O | $CH_3O$ | $CH_3O$ | N |
| Br | H | H | O | $CH_3$ | $OCH_3$ | CH |
| Br | H | H | O | $CH_3O$ | $CH_3$ | N |
| Br | H | H | O | $CH_3O$ | $CH_3O$ | CH |
| Br | H | H | S | $CH_3$ | $CH_3O$ | $CCH_3$ |
| F | H | H | O | $CH_3CH_2O$ | H | CH |
| F | H | H | O | $CH_3O$ | $CH_3$ | CH |
| F | H | H | O | $CH_3$ | $CH_3O$ | N |
| F | H | H | O | $CH_3O$ | $CH_3O$ | CH |
| $NO_2$ | H | H | O | $CH_3O$ | $CH_3$ | CH |
| $NO_2$ | H | H | O | $CH_3$ | $CH_3O$ | N |
| $NO_2$ | H | H | O | $CH_3O$ | $CH_3O$ | CH |
| $NO_2$ | 4-Cl | H | O | $CH_3O$ | $CH_3OCH_2$ | CH |
| $CH_3$ | 8-$NO_2$ | $CH_3$ | O | $CH_3$ | $CH_3CH_2OCH_2$ | N |
| $SO_2N(CH_3)(CH_3CH_2)$ | H | H | O | $CH_3$ | $CH_3O$ | CH |
| $SO_2N(CH_3CH_2)_2$ | H | H | O | $CH_3O$ | $CH_3O$ | CH |
| $SO_2N(CH_3)[CH(CH_3)_2]$ | H | H | O | $CH_3$ | $CH_3O$ | N |
| $SO_2N(CH_3)(CH_3CH_2CH_2)$ | H | H | O | $CH_3O$ | $CH_3CH_2CH_2$ | $CCH_3$ |
| $SO_2N[CH_2CH(CH_3)_2][CH(CH_3)_2]$ | 5-OH | H | S | $CH_3$ | $OCH_2CO_2CH_3$ | N |
| $SO_2N(CH_3)(OCH_3)$ | 6-Br | $CH_3$ | O | $CH_3O$ | $OCH_2CO_2CH_2CH_3$ | CH |
| $SO_2N(CH_3)(OCH_3)$ | H | H | O | $CH_3$ | $CH_3O$ | CH |
| $SO_2N(CH_3)(OCH_3)$ | H | H | O | $CH_3O$ | $CH_3O$ | CH |
| $OSO_2(CH_2CH_2CH_3)$ | H | H | O | $CH_3$ | $CH_3O$ | CH |
| $OSO_2(CH_2CH_3)$ | H | H | O | $CH_3O$ | $CH_3O$ | CH |
| $OSO_2(CH_2CH(CH_3)_2)$ | 3-Cl | H | S | $CH_3O$ | $\underset{CH_3}{OCHCO_2CH_2CH=CH_2}$ | N |
| $OSO_2(CH_3)$ | 7-F | H | O | $CH_3$ | $\underset{CH_3}{OCHCO_2CH_3}$ | CH |
| $O(CH_2CH_2CH_3)$ | 5-$OCH_3$ | H | O | $CH_3O$ | $OCH(CH_3)_2$ | CH |
| $O(CH_3)$ | H | $CH_3$ | O | $CH_3$ | $OCH_2CH_3$ | N |
| $O(CH_2CH_3)$ | H | H | O | $CH_3O$ | $CH_3O$ | CH |
| $O(CH(CH_3)CH_2CH_3)$ | H | H | O | $CH_3$ | $CH_3O$ | CH |
| $S(CH(CH_3)_2)$ | H | H | O | $CH_3$ | $CH_3O$ | CH |
| $S(CH_2CH(CH_3)_2)$ | H | H | O | $CH_3O$ | $CH_3O$ | CH |
| $S(CH_2CH_3)$ | 4-Br | H | S | $CH_3O$ | $O-CH_2CH=CH_2$ | CH |
| $SO_2(CH_3)$ | H | H | O | $CH_3O$ | $CH_3$ | CH |
| $SO_2(CH_3)$ | H | H | O | $CH_3O$ | $CH_3O$ | CH |
| $SO_2(CH_3)$ | H | H | O | $CH_3$ | $CH_3$ | CH |
| $SO_2(CH_3)$ | H | H | O | $CH_3$ | $CH_3$ | N |
| $SO_2(CH_3)$ | H | H | O | $CH_3$ | $CH_3O$ | N |
| $SO_2(CH_3)$ | H | H | O | $CH_3O$ | $CH_3O$ | N |

TABLE I-continued
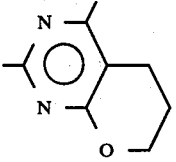
| A² | A¹ | R⁴ | W | X | Y | Z |
|---|---|---|---|---|---|---|
| OSO₂CF₃ | 8-Cl | H | O | CH₃ | OCH₂C(CH₃)=CH₂ | N |
TABLE II
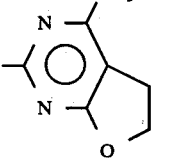
| A² | A¹ | R⁴ | W | R⁵ |
|---|---|---|---|---|
| Cl | H | H | O | 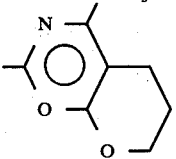 |
| Cl | H | H | O | 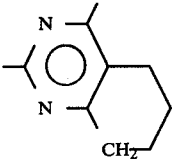 |
| Cl | H | H | O | 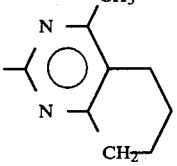 |
| Cl | H | H | O |  |
| Cl | H | H | O | 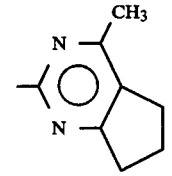 |
TABLE II-continued
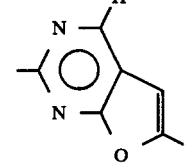
| A² | A¹ | R⁴ | W | R⁵ |
|---|---|---|---|---|
| Cl | H | H | O | 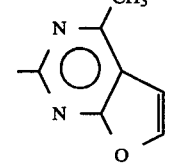 |
| Cl | H | H | O | 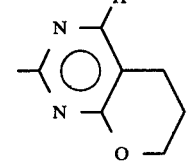 |
| Cl | H | H | O | 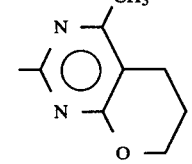 |
| SO₂(CH₃) | H | H | O |  |
| SO₂(CH₃) | H | H | O | |

TABLE II-continued

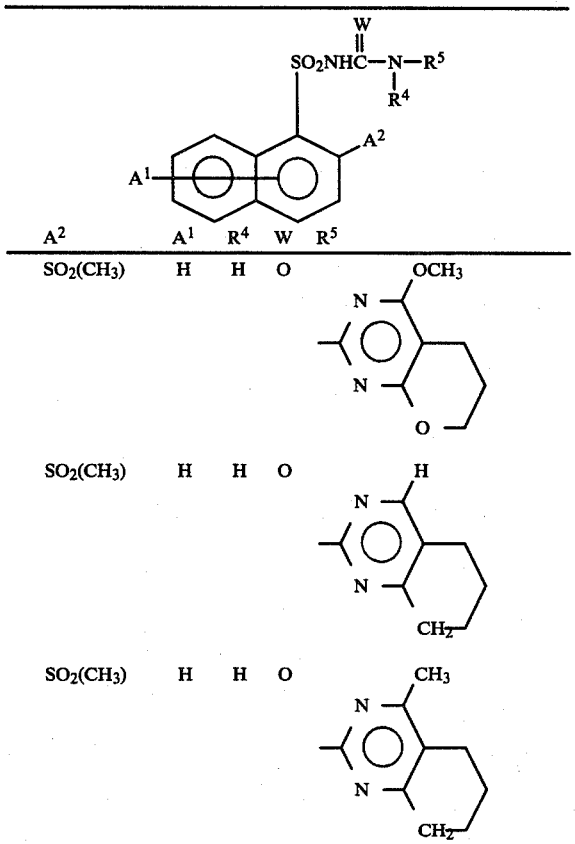

| A² | A¹ | R⁴ | W | R⁵ |
|---|---|---|---|---|
| SO₂(CH₃) | H | H | O | (4-methoxy-2,6-dimethylpyrimidinyl)propyl-O |
| SO₂(CH₃) | H | H | O | (2,6-dimethylpyrimidin-4-yl)-CH₂- |
| SO₂(CH₃) | H | H | O | (4,6-dimethylpyrimidin-5-yl)-CH₂- |

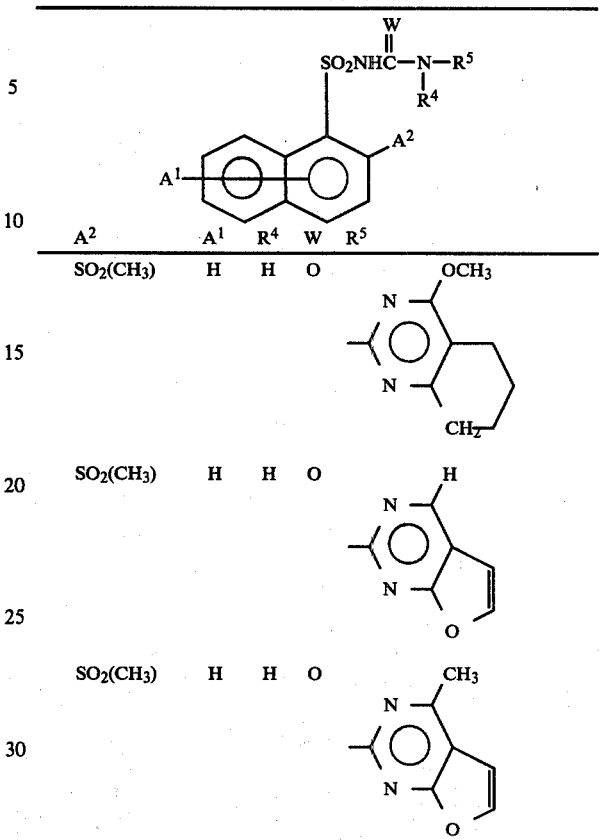

| A² | A¹ | R⁴ | W | R⁵ |
|---|---|---|---|---|
| SO₂(CH₃) | H | H | O | (4-methoxy-2,6-dimethylpyrimidin-5-yl)-CH₂- |
| SO₂(CH₃) | H | H | O | (2,6-dimethylpyrimidin-4-yl)-CH=CH-O- |
| SO₂(CH₃) | H | H | O | (4,6-dimethylpyrimidin-5-yl)-CH=CH-O- |

TABLE III

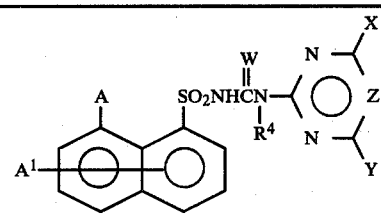

| A | A¹ | R⁴ | W | X | Y | Z | m.p. (°C.) |
|---|---|---|---|---|---|---|---|
| Cl | H | H | O | CH₃ | CH₃ | CH | |
| Cl | H | H | O | CH₃O | CH₃ | CH | 158–161° |
| Cl | H | H | O | CH₃O | CH₃O | CH | |
| Cl | H | H | O | CH₃ | CH₃ | N | |
| Cl | H | H | O | CH₃O | CH₃ | N | 98° |
| Cl | H | H | O | CH₃O | CH₃O | N | |
| NO₂ | H | H | O | CH₃ | CH₃ | CH | |
| NO₂ | H | H | O | CH₃O | CH₃ | CH | |
| NO₂ | H | H | O | CH₃O | CH₃O | CH | |
| NO₂ | H | H | O | CH₃ | CH₃ | N | |
| NO₂ | H | H | O | CH₃O | CH₃ | N | |
| NO₂ | H | H | O | CH₃O | CH₃O | N | |
| SO₂(CH₃) | H | H | O | CH₃ | CH₃ | N | |
| SO₂(CH₃) | H | H | O | CH₃O | CH₃ | N | |
| SO₂(CH₃) | H | H | O | CH₃O | CH₃O | N | |
| SO₂(CH₃) | H | H | O | CH₃ | CH₃ | N | |
| SO₂(CH₃) | H | H | O | CH₃O | CH₃ | N | |
| SO₂(CH₃) | H | H | O | CH₃O | CH₃O | N | |
| F | 7-CH₃O | H | S | CH₃ | CH₃O | CCH₃ | |
| F | 2-CH₃ | H | O | CH₃O | CH₃O | CH | |
| F | H | CH₃ | O | CH₃O | CH₃OCH₂ | CH | |
| Br | 3-CH₃O | H | S | CH₃ | CH₃CH₂OCH₂ | N | |
| Br | H | H | O | CH₃O | CH₃O | CH | |
| Br | 4-F | H | O | CH₃ | CH₃CH₂CH₂ | N | |
| CH₃ | 6-OCH₃ | H | O | CH₃ | OCH₂CO₂CH₃ | N | |
| CH₃ | 5-Cl | CH₃ | O | CH₃O | OCH₂CO₂CH₂CH₃ | CH | |
| CH₃ | H | H | S | CH₃O | CH₃ | N | |
| SO₂N(CH₃)(CH₂CH₃) | H | H | O | CH₃O | CH₃O | CH | |

TABLE III-continued

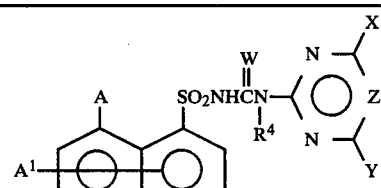

| A | A¹ | R⁴ | W | X | Y | Z | m.p. (°C.) |
|---|---|---|---|---|---|---|---|
| SO₂N(CH(CH₃)₂)(CH₂CH₃) | H | H | O | CH₃O | CH₃ | N | |
| SO₂N(CH₂CH(CH₃)₂)(CH₂CH₂CH₃) | 5-NO₂ | H | S | CH₃O | O—CH(CH₃)CO₂CH₂CH=CH₂ | N | |
| SO₂N(CH₂CH₃)₂ | 2-OCH₃ | H | O | CH₃ | O—C(CH₃)(CH₃)CO₂CH₃ | CH | |
| SO₂N(CH₃)(CH₂CH₂CH₂CH₃) | 4-Me | CH₃ | O | CH₃O | OCH₂CH₃ | CH | |
| SO₂N(OCH₃)CH₃ | H | H | O | CH₃O | CH₃O | CH | |
| SO₂N(OCH₃)CH₃ | H | H | O | CH₃O | CH₃ | CH | |
| SO₂N(OCH₃)CH₃ | 7-Cl | H | S | CH₃ | OCH(CH₃)₂ | N | |
| SO₂N(OCH₃)CH₃ | 5-NO₂ | CH₃ | O | CH₃O | OCH₂CH=CH₂ | CH | |
| OSO₂(CH₂CH₂CH₃) | 7-Br | H | O | CH₃ | OCH₂C(CH₃)=CH₂ | N | |
| OSO₂(CH(CH₃)CH₂CH₃) | 4-CH₃ | H | S | CH₃ | CH₃O | CCH₃ | |
| OSO₂(CH(CH₃)₂) | 3-CH₃O | H | O | CH₃O | CH₃O | CCH₃ | |
| OSO₂(CH₃) | H | H | O | CH₃O | CH₃ | N | |
| O(CH₂CH₃) | 7-NO₂ | H | O | CH₃ | OCH₃ | CH | |
| O(CH₃) | H | H | O | CH₃O | CH₃O | CH | |
| O(CH₂CH(CH₃)₂) | H | CH₃ | O | CH₃ | CH₃O | CH | |
| O(CH₂CH₂CH₂CH₃) | 4-Br | H | O | CH₃CH₂O | CH₂OCH₃ | N | |
| OSO₂CF₃ | H | H | O | CH₃O | CH₃ | CH | |
| OSO₂CF₃ | H | H | O | CH₃O | CH₃O | CH | |
| OSO₂CF₃ | 5-F | H | S | CH₃ | CH₃ | CCH₃ | |
| S(CH₃) | 2-F | H | S | CH₃O | CH₃ | N | |
| S(CH₃) | H | H | O | CH₃O | CH₃O | CH | |
| S(CH(CH₃)₂) | 5-OCH₃ | H | O | CH₃O | CH₃O | CH | |
| CO₂CH₃ | H | H | O | CH₃ | CH₃O | N | |
| CO₂C₂H₅ | H | H | O | CH₃ | C₂H₅O | N | |
| CO₂CH₂CH₂Cl | H | H | O | CH₃ | C₂H₅O | N | |
| CO₂CH₂CH=CH₂ | H | H | O | CH₃ | CH₃ | CH | |

TABLE IV

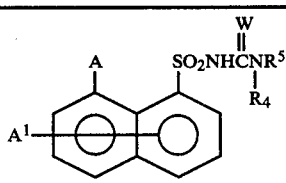

| A | A¹ | R⁴ | W | R⁵ |
|---|---|---|---|---|
| NO₂ | H | H | O | 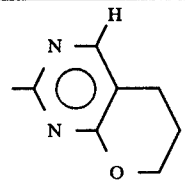 |
| NO₂ | H | H | O | 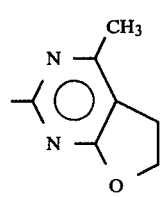 |

TABLE IV-continued

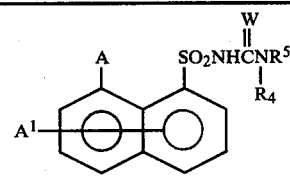

| A | A¹ | R⁴ | W | R⁵ |
|---|---|---|---|---|
| NO₂ | H | H | O | 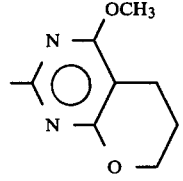 |
| NO₂ | H | H | O | |

TABLE IV-continued
| A | A¹ | R⁴ | W | R⁵ |
|---|----|----|----|----|
| NO₂ | H | H | O | 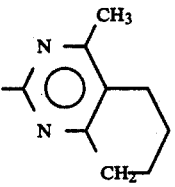 |
| NO₂ | H | H | O | 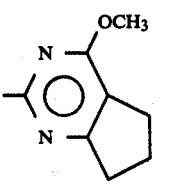 |
| NO₂ | H | H | O | 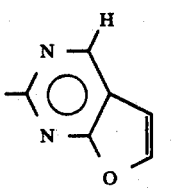 |
| NO₂ | H | H | O | 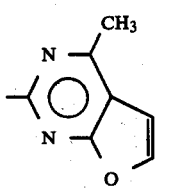 |
| SO₂(CH₃) | H | H | O | 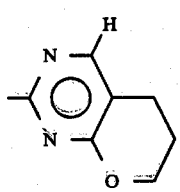 |
| SO₂(CH₃) | H | H | O | 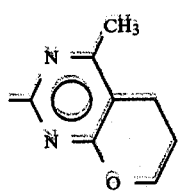 |
| SO₂(CH₃) | H | H | O | 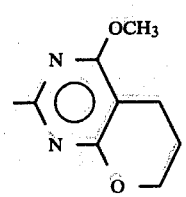 |
TABLE IV-continued
| A | A¹ | R⁴ | W | R⁵ |
|---|----|----|----|----|
| SO₂(CH₃) | H | H | O |  |
| SO₂(CH₃) | H | H | O | 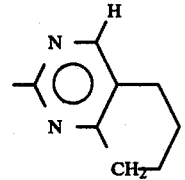 |
| SO₂(CH₃) | H | H | O | 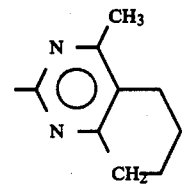 |
| SO₂(CH₃) | H | H | O | 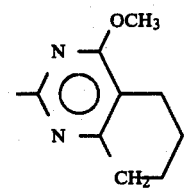 |
| SO₂(CH₃) | H | H | O | 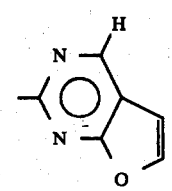 |
| Cl | H | H | O | 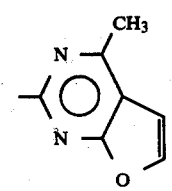 |
| Cl | H | H | O | 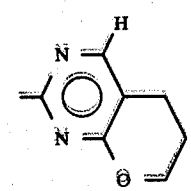 |

TABLE IV-continued

Structure: naphthalene with A at position 8, A¹ substituent, and SO₂NHC(=W)NR⁵R⁴ group at position 1.

| A | A¹ | R⁴ | W | R⁵ |
|---|----|----|----|----|
| Cl | H | H | O | pyrimidine with CH₃O, CH₂, O substituents |
| Cl | H | H | O | pyrimidine with H, CH₂ substituents |
| Cl | H | H | O | pyrimidine with CH₃, CH₂ substituents |
| Cl | H | H | O | pyrimidine with CH₃O, CH₂ fused to furan |
| Cl | H | H | O | pyrimidine with H, fused to furan |
| Cl | H | H | O | pyrimidine with CH₃, fused to furan |

TABLE V

Structure: naphthalene (with A¹ and A² substituents) bearing SO₂N=C(NR⁴)(WR₆) linked to a 6-membered ring with N, N, X, Y, Z substituents.

| A² | A¹ | R⁴ | W | R⁶ | X | Y | Z |
|----|----|----|---|-----|---|---|---|
| Cl | H | H | O | CH₃ | CH₃CH₂O | H | CH |
| Cl | H | H | O | CH₃ | CH₃ | CH₃O | CCH₃ |
| Cl | H | H | S | CH₃CH₂ | CH₃O | CH₃OCH₂ | N |
| Cl | H | H | S | CH₃ | CH₃ | CH₃O | CH |
| Cl | H | H | S | CH₃cH₂ | CH₃ | CH₃O | N |
| Cl | H | H | S | CH₃ | CH₃O | CH₃O | CH |
| Br | 8-NO₂ | H | S | CH₂CH=CH₂ | CH₃ | CH₃CH₂OCH₂ | N |
| Br | 8-NO₂ | H | S | CH₃<br>\|<br>CH₂CHCH₃ | CH₃ | OCH₂CO₂CH₃ | N |
| Br | H | H | O | CH₃ | CH₃ | CH₃O | CH |
| F | 5-OCH₃ | H | S | CH₂CH₂CH₂CH₂CH₃ | CH₃ | CH₃ | N |
| F | H | H | S | CH₃ | CH₃O | CH₃O | CH |
| F | H | H | S | CH₂CH₂CH=CH₂ | CH₃ | CH₃ | CH |
| NO₂ | 4-Cl | H | S | cyclohexenyl | CH₃O | CH₃O | N |
| NO₂ | H | H | S | CH₃ | CH₃O | CH₃ | CH |
| NO₂ | H | H | S | cyclopentyl | CH₃ | OCH₂CO₂CH₂CH₃ | CH |

TABLE V-continued

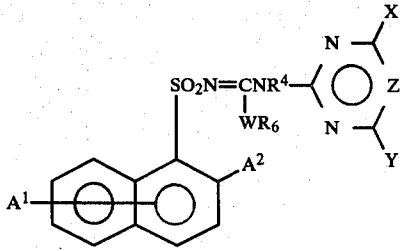

| A² | A¹ | R⁴ | W | R⁶ | X | Y | Z |
|---|---|---|---|---|---|---|---|
| CH₃ | 5-NO₂ | H | S | CH₃ | CH₃ | CH₃CH₂OCH₂ | N |
| CH₃ | H | H | S | CH₃ | CH₃O | CH₃O | CH |
| CH₃ | 8-NO₂ | H | S | CH₃ | CH₃O | CH₃CH₂CH₂ | CH |
| SO₂N(CH₃)(OCH₃) | 6-Br | H | O | CH₃ | CH₃O | CH₃ | N |
| SO₂N(CH₃)(OCH₃) | 5-OCH₃) | H | S | CH₃ | CH₃O | CH₃ | CCH₃ |
| SO₂N(CH₃)(OCH₃) | H | H | S | CH₃ | CH₃O | CH₃O | CH |
| OSO₂(CH₂CH(CH₃)₂) | 3-Cl | H | S | CH₃ | CH₃ | CH₃CH₂OCH₂ | CH |
| OSO₂(CH₂CH₃) | 7-F | H | S | CH₃CH₂CH₂ | CH₃CH₂O | CH₃ | N |
| OSO₂(CH₃) | H | H | S | CH₃CH₂ | CH₃ | CH₃O | N |
| O(CH₃) | 3-Cl | H | S | CH₃ | CH₃ | CH₃O | CH |
| O(CH₃CH₂) | H | H | S |  | CH₃O | CH₃O | CH |
| O(CH₃) | H | H | S | CH₂CH=CH₂ | CH₃ | CH₃ | N |
| S(CH₃) | 4-Br | H | S | CH₃ | CH₃CH₂O | CH₃ | N |
| S(CH₃CH₂) | H | H | O | CH₃ | CH₃ | CH₃O | N |
| S(CH₃) | H | H | S | CH₂CH=CHCH₃ | CH₃ | OCHCO₂H<br>\|<br>CH₃ | CH |
| SO₂(CH₃) | H | H | S | CH₃ | CH₃O | CH₃ | CH |
| SO₂(CH₃) | H | H | O | CH₃ | CH₃O | CH₃ | N |
| SO₂(CH₃) | H | H | S | CH₃CH₂ | CH₃O | CH₃O | N |
| SO₂(CH₃CH₂CH₂CH₂) | H | H | S | CH₃ | CH₃CH₂O | CH₃CH₂OCH₂ | CH |
| SO₂(CH₂CH₃) | H | H | S | CH₂CH=CH₂ | CH₃O | CH₃OCH₂ | CH |
| SO₂(CH(CH₃)₂) | 4-Br | H | S |  | CH₃ | OCH₂CO₂CH₂CH₃ | CH |
| OSO₂CF₃ | H | H | S | CH₃ | CH₃O | CH₃ | CH |
| OSO₂CF₃ | H | H | S | CH(CH₃)₂ | CH₃O | CH₃ | N |
| SO₂N(CH₃)(CH₂CH₃) | 6-Br | H | S | CH₃ | CH₃O | CH₃ | CH |
| SO₂N(CH₃CH₂)((CH₃)₂CH) | H | H | O | CH₂CH₃ | CH₃ | CH₃OCH₂ | CH |
| SO₂N(CH₃CH₂)(CH₃) | H | H | S | CH₃ | CH₃O | CH₃O | CH |
| SO₂N(CH₃CH₂CH₂CH₂)(CH₃) | H | H | S | CH₃ | CH₃ | CH₃O | N |

TABLE VI

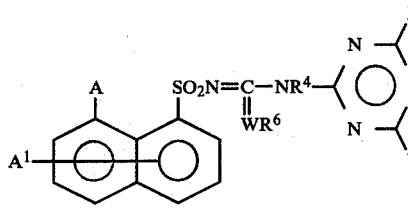

| A | A¹ | R⁴ | W | R⁶ | X | Y | Z |
|---|---|---|---|---|---|---|---|
| Cl | H | H | O | CH₃ | CH₃ | CH₃O | CH |
| Cl | H | H | S | CH₃ | CH₃ | CH₃O | N |
| Cl | H | H | S | CH₂—CH=CH₂ | CH₃O | CH₃O | N |
| Cl | H | H | S |  | CH₃O | CH₃O | CH |
| Cl | H | H | O | CH₃ | CH₃ | CH₃CH₂OCH₂ | CH |
| Cl | H | H | S | CH₃ | CH₃CH₂O | CH₃ | CCH₃ |
| Br | 7-OCH₃ | H | S | (CH₃)₂CH | CH₃O | CH₃OCH₂ | CH |
| Br | H | H | O | CH₃ | CH₃ | CH₃O | CH |

TABLE VI-continued

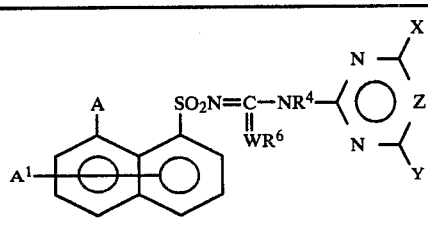

| A | A¹ | R⁴ | W | R⁶ | X | Y | Z |
|---|---|---|---|---|---|---|---|
| Br | 4-NO₂ | H | S | CH₃ | CH₃ | CH₃ | CH |
| F | 2-CH₃ | H | S | CH₃ | CH₃O | CH₃ | N |
| F | H | H | S | CH₂CH=CHCH₃ | CH₃ | OCH₂CO₂CH₃ | CH |
| F | H | H | S | -⟨cyclopentyl⟩ | CH₃ | OCH₂CO₂H | CH |
| CH₃ | 6-OCH₃ | H | O | CH₃ | CH₃O | CH₃ | N |
| CH₃ | 5-Cl | H | S | CH₃CH₂ | CH₃O | CH₃CH₂OCH₂ | CH |
| CH₃ | H | H | S | CH₃CH₂CH₂ | CH₃CH₂O | CH₃ | CCH₃ |
| NO₂ | H | H | S | CH₃ | CH₃O | CH₃ | N |
| NO₂ | H | H | S | CH₃ | CH₃O | CH₃O | CH |
| NO₂ | H | H | S | CH₃ | CH₃O | CH₃ | CH |
| NO₂ | 4-OCH₃ | H | S | CH₂CH(CH₃)₂ | CH₃O | OCH₂CO₂CH₃ | CH |
| NO₂ | 7-Cl | H | S | CH₃ | CH₃O | CH₃CH₂CH₂ | CH |
| NO₂ | 4-Br | H | S | CH₃ | CH₃ | CH₃<br>  \|<br>OCHCO₂CH₃ | CH |
| SO₂(CH₃) | H | H | O | CH₂CH₃ | CH₃O | CH₃ | CH |
| SO₂(CH₃) | H | H | S | CH₃ | CH₃O | CH₃O | CH |
| SO₂(CH₃) | H | H | S | CH₃ | CH₃O | CH₃O | N |
| SO₂(CH(CH₃)₂) | 3-OCH₃ | H | S | CH₂CH₃ | CH₃ | CH₃O | CH |
| SO₂(CH₂CH₃) | 2-F | H | S | CH₂CH=CH₂ | CH₃CH₂O | CH₃O | N |
| SO₂(CH₂CH₂CH₂CH₃) | 7-Cl | H | S | CH₃ | CH₃O | CH₃O | CH |
| SO₂(CH₃) | 5-OCH₃ | H | O | -⟨cyclohexyl⟩ | CH₃ | CH₃O | N |
| SO₂(CH₃) | H | H | S | CH₃ | CH₃O | CH₃ | CH |
| SO₂(CH₂CH₃) | 2-CH₃ | H | S | CH₃ | CH₃O | OCH₂OCH₂CH₃ | CH |
| SO₂(CH₃) | 7-NO₂ | H | O | CH₃ | CH₃O | CH₃<br>  \|<br>OCHCO₂CH₃ | N |
| SO₂(CH₃) | H | H | S | CH₃ | CH₃ | CH₃O | CH |
| SO₂(CH(CH₃)₂) | 5-Br | H | S | CH₂CH₂CH₂CH₃ | CH₃O | CH₃O | N |
| SO₂(CH₃) | 7-Br | H | S | CH₃ | CH₃O | OCH₂CO₂CH₃ | N |
| SO₂(CH₃) | H | H | S | CH₃ | CH₃O | CH₃ | CH |
| SO₂(CH₂CH₂CH₃) | 3-CH₃O | H | S | CH₃<br>  \|<br>CH₂CHCH₃ | CH₃O | OCH₂CH₃ | N |
| SO₂(CH₃) | H | H | S | CH₃ | CH₃ | CH₃O | N |
| SO₂(CH₃) | 4-CH₃ | H | S | CH₃ | CH₃O | CH₃O | CH |
| SO₂(CH₃) | H | H | O | CH₃ | CH₃O | CH₃ | CH |
| SO₂N(OCH₃)(CH₃) | H | H | S | CH₃ | CH₃ | CH₃O | CH |
| SO₂N(OCH₃)(CH₃) | H | H | S | CH₃ | CH₃O | CH₃O | CCH₃ |
| SO₂N(OCH₃)(CH₃) | H | H | S | CH₂CH₃ | CH₃O | CH₃ | N |
| SO₂N(CH₃)(CH₂CH₃) | H | H | S | CH₃ | CH₃O | CH₃OCH₂ | CH |
| SO₂N(CH₃CH₂CH₂)(CH₃) | H | H | S | CH₃ | CH₃ | CH₃O | N |
| SO₂N(CH₃CH₂CH₂CH₂)(CH₂CH₂CH₃) | H | H | S | CH₃ | CH₃O | CH₃O | CH |

TABLE VII

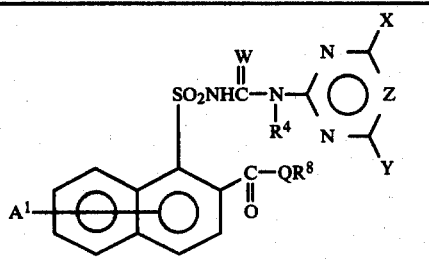

| QR⁸ | A¹ | W | R⁴ | X | Y | Z |
|---|---|---|---|---|---|---|
| OCH₃ | H | O | H | CH₃ | H | CH |
| OCH₃ | 8-F | O | H | H | CH₃ | CH |
| OCH₃ | 8-Cl | O | H | OCH₃ | OCH₃ | N |
| N(CH₃)₂ | 8-Br | O | H | CH₃ | OCH₃ | CH |
| N(CH₃)₂ | 8-NO₂ | O | H | CH₃ | OCH₃ | CH |
| OCH₃ | 5-CH₃ | O | H | CH₃ | OCH₃ | CCH₃ |
| OCH₃ | 5-CH₃ | O | H | CH₃ | CH₃ | CCH₃ |
| OCH₂CH₂OCH₃ | 5-Cl | O | H | CH₃ | OC₂H₅ | CH |
| OC₂H₅ | 6-Cl | S | H | CH₃ | CH₂OCH₃ | CH |
| SCH₃ | H | O | H | CH₃ | OCH₂OC₂H₅ | N |
| SCH₃ | H | S | H | CH₃ | OCH₂OCH₃ | N |
| OC₂H₅ | H | S | H | CH₃ | OCH(CH₃)CO₂CH₃ | CH |
| OC₂H₅ | H | O | H | CH₃ | OCH₂CO₂CH₃ | CH |
| OC₂H₅ | H | O | H | CH₃ | OCH₂CO₂C₂H₅ | CH |
| OCH₃ | H | O | CH₃ | OCH₃ | OCH₃ | N |
| OC₂H₅ | H | O | CH₃ | OCH₃ | N(CH₃)₂ | N |
| OCH₃ | 5-Cl | O | CH₃ | OCH₃ | CH₃ | CH |
| SCH₂CH₂OCH₂CH₃ | 6-Cl | O | CH₃ | OCH₃ | OC₂H₅ | CCH₃ |
| SCH₃ | 3-CH₃ | O | CH₃ | OCH₃ | OCH₃ | N |
| OCH₃ | H | O | H | CH₃ | OCH₂COOCH₃ | CH |
| OCH₂CH₂Cl | H | O | H | OCH₃ | OCH₂COOC₂H₅ | CH |
| OCH₃ | H | O | H | CH₃ | OCH₂COOC₂H₅ | CH |
| O—n-C₃H₇ | H | S | H | OCH₃ | CH₃ | CH |
| N—(C₃H₇)₂ | H | S | H | OCH₃ | OCH₃ | CH |
| S—C₂H₅ | H | O | H | OCH₃ | CH₃ | CH |
| O—CH(CH₃)CH₂CH₃ | H | O | H | OCH₃ | CH₃ | CH |
| O—CH(CH₃)CH₂CH₃ | H | O | H | OCH₃ | OCH₃ | N |
| OCH₂CH₂Cl | H | O | H | OCH₃ | CH₃ | CCH₃ |
| OCH₂CH₂Cl | H | O | H | OCH₃ | OCH₃ | CH |
| O(CH₂)₅CH₃ | H | O | H | OCH₃ | CH₃ | CH |
| O(CH₂)₅CH₃ | H | O | H | OCH₃ | OCH₃ | N |
| O—⟨S⟩ | H | O | H | OCH₃ | OCH₃ | N |
| OCH₃ | 4-Cl | S | H | OCH₃ | CH₃ | N |
| OCH₃ | 4-Cl | S | H | OCH₃ | OCH₃ | N |
| O—i-C₃H₇ | H | O | H | OCH₃ | CH₃ | N |
| O—i-C₃H₇ | H | O | H | OCH₃ | OCH₂CH=CH₂ | N |
| O—n-C₄H₉ | H | O | H | OCH₃ | CH₃ | CCH₃ |
| O—n-C₄H₉ | H | O | H | OCH₃ | OCH₃ | CCH₃ |
| OC₂H₅ | H | O | H | OCH₃ | OCH₃ | CH |
| O(CH₂)₅CH₃ | H | O | H | CH₃ | OCH₂CO₂CH₃ | CH |
| OCH(CH₂)₄CH₃ | H | O | H | CH₃ | CH₃ | CH |
| OCH₂—⟨Ph⟩ | H | O | H | CH₃ | OCH₃ | CH |
| OCH₂—⟨Ph⟩—CH₃ | H | O | H | CH₃ | OCH₃ | CH |
| OCH₂—⟨Ph⟩(CH₃)(Cl) | H | O | H | CH₃ | OCH₃ | CH |

TABLE VII-continued

| QR8 | A1 | W | R4 | X | Y | Z |
|---|---|---|---|---|---|---|
| O—CH2—(2,5-dimethoxy... ring with CH3, OCH3) | H | O | H | CH3 | OCH3 | CH |
| O—CH2—(ring with Cl, OCH3) | H | O | H | CH3 | OCH3 | CH |
| O—(phenyl) | H | O | H | CH3 | OCH3 | CH |
| O—(phenyl-Cl, Cl) | H | O | H | CH3 | OCH3 | CH |
| O—(phenyl-Cl, CH3) | H | O | H | CH3 | OCH3 | CH |
| O—(phenyl-CH3, OCH3) | H | O | H | CH3 | OCH3 | N |
| (phenyl-CH3, CH3) | H | O | H | CH3 | OCH3 | N |
| NCH2—(phenyl), H | H | O | H | CH3 | OCH3 | CH |
| SCH2—(phenyl) | H | O | H | CH3 | OCH3 | CH |
| NH—(phenyl) | H | O | H | CH3 | OCH3 | CH |
| N(CH3)—(phenyl) | H | O | H | CH3 | OCH3 | CH |
| S—(phenyl-Cl) | H | O | H | CH3 | OCH3 | N |
| —S—(phenyl-OCH3) | H | O | H | CH3 | OCH3 | N |

TABLE VII-continued

![Structure with SO2NHC(=W)-N(R4)- attached to naphthalene with A1 and C(=O)QR8, linked to pyrimidine ring with X, Y, Z]

| QR8 | A¹ | W | R⁴ | X | Y | Z |
|---|---|---|---|---|---|---|
| —NH—(2,4-dichlorophenyl) | H | O | H | CH₃ | OCH₃ | N |
| —NH—(2-OCH₃, 5-OCH₃-phenyl) | H | O | H | CH₃ | OCH₃ | N |

TABLE VIII

![Structure with SO2N=C(WR6)-NH- attached to naphthalene with A1 and CQR8(=O), linked to ring with X, Y, Z]

| A¹ | R⁶ | QR⁸ | X | Y | W | Z |
|---|---|---|---|---|---|---|
| 5-Cl | CH₃ | OCH₃ | CH₃ | H | S | N |
| 6-Cl | CH₃ | OCH₃ | OCH₃ | OCH₃ | S | N |
| 6-Br | CH₃ | OCH₃ | CH₃ | OCH₃ | S | N |
| 5-Br | CH₃ | OC₂H₅ | CH₃ | OCH₃ | S | N |
| 8-Br | CH₃ | OC₂H₅ | OCH₃ | OCH₃ | O | N |
| 5-F | CH₃ | OCH₃ | CH₃ | CH₂OCH₃ | O | N |
| H | CH₂CH₃ | OC₃H₇ | CH₃ | OC₂H₅ | S | N |
| 4-F | CH₃ | OC₃H₇ | CH₃ | OCH₃ | S | CH |
| 8-CH₃ | CH₃ | OCH₃ | CH₃ | CH₂OCH₃ | S | CH |
| 5-NO₂ | CH₃ | OC₄H₉ | CH₃ | N(CH₃)₂ | O | CH |
| 4-CH₃ | CH₃ | O-cyclohexyl | CH₃ | OCH₃ | S | CH |
| 4-C₂H₅ | CH₃ | O-phenyl | CH₃ | OCH₂CH₂CH₃ | S | CH |
| 8-Cl | CH₂CH₂CH₃ | N(CH₃)₂ | CH₃ | OCH₃ | S | CCH₃ |
| 6-Cl | CH₃ | N(CH₃)₂ | CH₃ | OCH₃ | S | CCH₃ |
| 8-CH₃ | CH₃ | SCH₃ | CH₃ | OCH₃ | S | CH |
| 4-CH₃ | CH₃ | SCH₃ | CH₃ | CH₂OCH₃ | S | CH |
| 5-Cl | CH₃ | OCH₃ | CH₃ | H | S | N |
| 6-Cl | CH₃ | OCH₃ | H | OCH₂CH=CH₂ | S | N |
| 6-Cl | CH₃ | OCH₃ | OCH₃ | OCH₃ | S | N |
| 6-Br | CH₃ | OCH₃ | CH₃ | OCH₃ | S | N |
| 5-Br | CH₃ | —N(piperidine) | CH₃ | OCH₃ | S | N |
| 5-Br | CH₃ | OCH₃ | OCH₃ | OCH₃ | S | N |
| 3-Br | CH₃ | OCH₃ | OCH₃ | OCH₃ | S | N |

TABLE VIII-continued

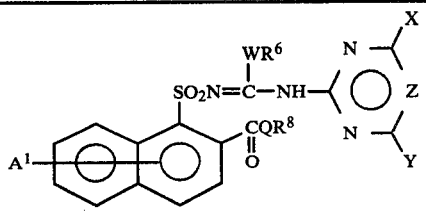

| A¹ | R⁶ | QR⁸ | X | Y | W | Z |
|---|---|---|---|---|---|---|
| H | CH₃ | OCH₃ | CH₃ | OC₂H₅ | S | N |
| 3-F | CH₃ | OCH₃ | CH₃ | OCH₃ | S | N |
| 5-F | CH₃ | OCH₃ | CH₃ | CH₂OCH₃ | S | N |
| H | CH₃ | OCH₃ | CH₃ | CH₂OCH₃ | S | CH |
| 6-F | CH₂CH₃ | OCH₃ | CH₃ | OCH₂CH₃ | S | CH |
| 5-NO₂ | CH₃ | OCH₃ | CH₃ | N(CH₃)₂ | S | CH |
| 4-CH₃ | CH₃ | OCH₃ | CH₃ | OCH₃ | S | CCH₃ |
| H | CH₃ | OCH₃ | CH₃ | CH₃ | S | CH |
| 2-Cl | CH₂CH=CH₂ | OCH₃ | CH₃ | OCH₃ | S | CH |
| 6-Cl | CH₃ | OCH₃ | CH₃ | OCH₃ | S | CH |
| 2-CH₃ | CH₃ | OCH₃ | CH₃ | OCH₃ | S | CH |
| 4-CH₃ | CH₃ | OCH₃ | CH₃ | OCH₂OCH₃ | S | CH |
| 6-Cl | CH₃ | OCH₃ | CH₃ | CH₃ | S | CH |
| 6-Cl | CH₃ | OCH₃ | OCH₃ | OCH₃ | S | N |
| 5-CH₃ | CH₃ | OCH₃ | CH₃ | OCH₃ | S | N |
| 6-CH₃ | CH₂CH=CH₂ | OCH₃ | CH₃ | OCH₂CO₂CH₃ | S | N |
| 5-Br | CH₃ | OCH₃ | CH₃ | OCH₂CO₂CH₃ | S | N |
| 5-CH₃ | CH₃ | OCH₃ | CH₃ | CH₃ | S | N |
| 5-NO₂ | CH₃ | OCH₃ | CH₃ | OCH₂CH₃ | S | CH |
| 4-Cl | CH₃ | OCH₃ | CH₃ | N(CH₃)₂ | S | CH |
| 6-CH₃ | CH₂CH₂CH₂CH₂CH₃ | OCH₃ | CH₃ | OCH₂CH=CH₂ | S | CCH₃ |
| 4-F | CH₃ | OCH₃ | CH₃ | OCH₂CO₂C₂H₅ | S | CH |
| 5-NO₂ | CH₃ | OCH₃ | OCH₃ | OCH₃ | S | CH |
| 5-Br | CH₃ | OCH₃ | OCH₃ | OCH₃ | S | N |
| 5-NO₂ | CH₂CH=CH₂CH₃ | OCH₃ | CH₃ | OCH₃ | S | N |
| 5-F | CH₃ | OCH₃ | OC₂H₅ | CH₂OCH₃ | S | N |
| 2-Cl | CH₃ | OCH₃ | OCH₃ | OCH₃ | S | N |
| 2-Cl | CH₃ | OCH₃ | CH₃ | OCH₃ | S | N |
| 2-CH₃ | CH₃ | OCH₃ | CH₃ | OCH₂OCH₃ | S | N |
| 3-Cl | CH₃ | OCH₃ | CH₃ | OCH₂CO₂CH₃ | S | N |
| 3-H | CH₃ | OCH₃ | OCH₃ | OCH₃ | S | N |
| 3-Cl | CH₃ | OCH₃ | CH₃ | CH₃ | S | N |

TABLE IX

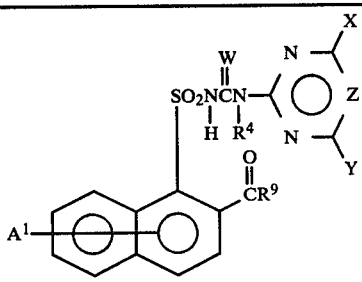

| A¹ | R⁹ | R⁴ | W | X | Y | Z |
|---|---|---|---|---|---|---|
| H | CH₃ | H | O | CH₃O— | CH₃O— | CH |
| H | CH₃ | H | O | CH₃O— | CH₃O— | CH |
| H | CH₃ | H | O | CH₃— | CH₃— | N |
| H | CH₃ | CH₃ | O | CH₃O— | CH₃— | CH |
| H | CH₃ | H | S | CH₃O— | CH₃O— | N |
| 8-CH₃ | CH₃ | H | O | CH₃O— | CH₃O— | CH |
| 5-Cl | CH₃ | H | O | CH₃O— | CH₃— | CH |
| 8-Cl | CH₃ | H | S | CH₃O— | CH₃O— | CH |
| 8-NO₂ | CH₃ | H | O | CH₃— | CH₃— | N |
| 8-F | CH₃ | H | O | CH₃O— | CH₃— | CCH₃ |
| 5-Br | CH₃ | H | O | CH₃O— | CH₃— | CCH₃ |
| 5-NO₂ | CH₃ | H | O | CH₃O— | CH₃O— | N |
| H | C₂H₅ | H | O | CH₃O— | CH₃O— | CH |
| H | C₂H₅ | H | S | CH₃O— | CH₃O— | CH |
| H | C₂H₅ | CH₃ | O | CH₃O— | CH₃— | CH |
| 8-CH₃ | C₂H₅ | H | O | CH₃O— | CH₃O— | CH |
| H | CH₃ | H | O | CH₃CH₂O— | CH₃— | CH |
| H | C₂H₅ | H | O | CH₃ | CH₃— | N |
| H | CH₃—CH₂— | H | O | CH₃— | CH₃O— | N |

TABLE IX-continued

![Structure showing naphthalene with SO2NCN-R4 sulfonylurea-like linkage to pyrimidine with X, Y, Z substituents, and COR9 group, with A1 on naphthalene]

| A¹ | R⁹ | R⁴ | W | X | Y | Z |
|---|---|---|---|---|---|---|
| H | CH₃CH₂CH₂— | H | O | CH₃O— | CH₃O— | N |
| H | CH₃OCH₂— | H | O | CH₃— | CH₃O— | N |
| H | cyclohexyl— | H | O | CH₃O— | CH₃O— | N |
| H | C₆H₅CH₂— | H | O | CH₃O— | CH₃O— | CH |
| H | C₆H₅CH₂— | H | O | CH₃O— | CH₃O— | CH |
| 4-Cl | CH₃CH₂CH₂— | H | O | CH₃O— | CH₃— | N |
| 8-Cl | CH₃CH₂CH₂— | H | S | CH₃O— | CH₃O— | CH |
| 8-NO₂ | C₆H₅CH₂— | H | O | CH₃O— | CH₃O— | C—CH₃ |
| 8-CH₃ | CH₃ | H | O | CH₃— | CH₃CH₂CH₂O— | N |
| H | CH₃ | H | O | CH₃— | C₂H₅OCCH₂— | CH |
| H | CH₃OCH₂— | H | O | CH₃O— | CH₃O— | CH |
| H | CH₃OCH₂— | H | O | CH₃O— | CH₃— | N |
| H | cyclohexyl-CH₂— | H | O | CH₃O— | CH₃O— | CH |

Additional analogs of Table IX wherein

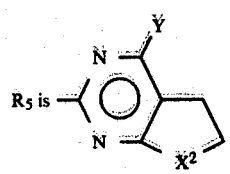

R₅ is can be made by methods taught herein.

TABLE X
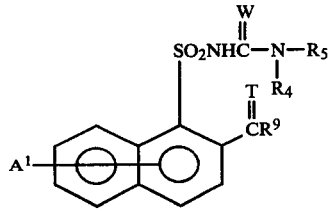
| A¹ | T | R⁹ | W | R⁴ | R⁵ |
|---|---|---|---|---|---|
| H | NOCH₃ | CH₃ | O | CH₃ | 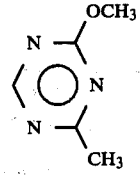 |
| H | NOC₂H₅ | 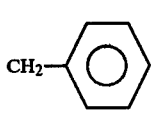 | O | H | 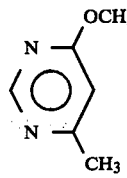 |
| H | NOCH(CH₃)₂ | (CH₂)₅CH₃ | O | H | 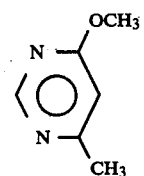 |
| H | NOCH₂CH=CH₂ | CH₂CH=CH₂ | O | CH₃ | 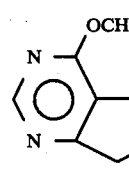 |
| H | NOCH₂CH=CHCH₃ | CH₂CH=CH—CH₃ | O | H | 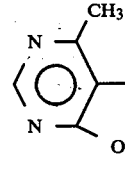 |
| H | NOCH₂CH=CH(CH₂)₂CH₃ | CH₂CH=CH(CH₂)₂CH₃ | O | H | 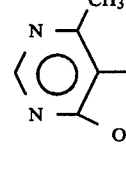 |
| H | NOCH₃ |  | O | H | 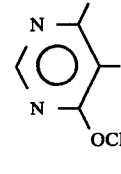 |
| H | NOCH(CH₃)₂ | 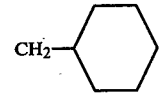 | O | H | 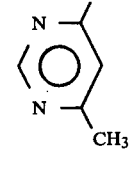 |

TABLE X-continued
| A¹ | T | R⁹ | W | R⁴ | R⁵ |
|---|---|---|---|---|---|
| H | NOCH₃ | 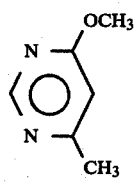 | O | H | 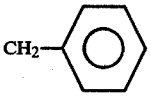 |
| H | NOCH₂CH=CH₂ | 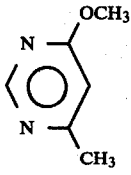 | O | H | 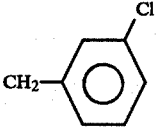 |
| H | NOCH₃ | 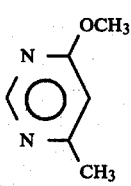 | O | H | 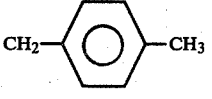 |
| H | NOCH₃ | 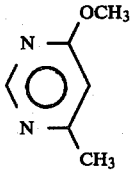 | O | H | 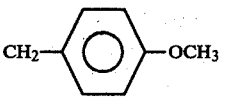 |
| H | NOCH₃ | 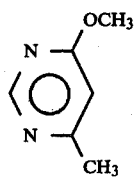 | O | H | 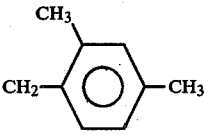 |
| H | NOCH₃ | 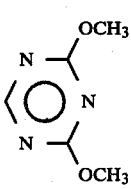 | O | CH₃ | 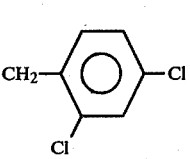 |
| H | NOCH₃ | 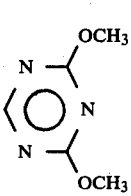 | O | CH₃ | |

TABLE X-continued $$\text{SO}_2\text{NHC}(=W)-N(R_4)-R_5 \text{ on naphthalene with } A^1, T, \text{ and } CR^9(=T) \text{ substituents}$$

| $A^1$ | T | $R^9$ | W | $R^4$ | $R^5$ |
|---|---|---|---|---|---|
| H | NOCH$_3$ | CH$_2$-(phenyl-4-OCH$_3$, 3-Cl) | O | CH$_3$ | 2-(4,6-dimethoxypyrimidinyl) |
| H | NOCH$_3$ | CH$_2$-(phenyl-3-CH$_3$, 4-OCH$_3$) | O | CH$_3$ | 2-(4,6-dimethoxypyrimidinyl) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High-strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE X

| | Active* Ingredient | Diluent(s) | Surfactant(s) |
|---|---|---|---|
| Wettable Powders | 20-90 | 0-74 | 1-10 |
| Oil Suspensions, Emulsions, Solutions (including Emulsifiable Concentrates | 3-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High-Strength Compositions | 90-99 | 0-10 | 0-2 |

*Active ingredient plus at least one of a surfactant or a diluent 100 weight percent.

Lower or higher levels of active ingredient can, of course, be present depending on the intended use and the physical properties of the compound. Higher ratios of surfactant to active ingredient are sometimes desirable, and areachieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, March 14, 1967, Col. 5, line 43 through Col. 1, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, June 23, 1959, Col. 5, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

Wettable Powder

| | |
|---|---|
| 2-Chloro-N—[(4,6-dimethylpyrimidin-2-yl)-aminocarbonyl]-1-naphthalene-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 7

Wettable Powder

| | |
|---|---|
| 2-Chloro-N—[(4,6-dimethoxypyrimidin-2-yl)-aminocarbonyl]-1-naphthalene-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 8

Granule

| | |
|---|---|
| wettable powder of Example 7 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 9

Extruded Pellet

| | |
|---|---|
| 2-Chloro-N—[(4-methoxy-6-methylpyrimidin-2-yl)-aminocarbonyl]-1-naphthalene-sulfonamide | 25% |
| anhydrous sodium sulfate | 10% |
| crude calcium ligninsulfonate | 5% |
| sodium alkylnaphthalenesulfonate | 1% |
| calcium/magnesuim bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Oil Suspension

| | |
|---|---|
| 2-Chloro-N—[(4,6-dimethyl-1,3,5-triazin-2-yl)-aminocarbonyl]-1-naphthalene-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

| | |
|---|---|
| 2-Chloro-N—[(4,6-dimethoxy-1,3,5-triazin-2-yl)-aminocarbonyl]-1-naphthalene-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

| | |
|---|---|
| 2-Chloro-N—[(4-methoxy-6-methyl-1,3,5-triazin-2-yl)aminocarbonyl]-1-naphthalene-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

| | |
|---|---|
| 2-Chloro-N—[(4,6-dimethoxypyrimidin-2-yl)aminocarbonyl]-1-naphthalene-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 14

Solution

| | |
|---|---|
| 2-Chloro-N—[(4-methoxy-6-methylpyrimidin-2-yl)-aminocarbonyl]-1-naphthalene-sulfonamide, sodium salt | 5% |
| water | 95% |

The salt is added directly to the water with stirring to produce the solution, which may then be packaged for use.

EXAMPLE 15

Low Strength Granule

| | |
|---|---|
| 2-Chloro-N—[(4,6-dimethyl-1,3,5-triazin-2-yl)-aminocarbonyl]-1-naphthalene-sulfonamide | 0.1% |
| attapulgite granules (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 16

Granule

| | |
|---|---|
| 2-Chloro-N—[(4,6-dimethoxypyrimidin-2-yl)-aminocarbonyl]-1-naphthalene-sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 17

High Strength Concentrate

| | |
|---|---|
| 2-Chloro-N—[(4,6-dimethylpyrimidin-2-yl)aminocarbonyl]-1-naphthalene-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 18

Wettable Powder

| | |
|---|---|
| 2-Chloro-N—[(4,6-dimethylpyrimidin-2-yl)aminocarbonyl]-1-naphthalene-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 19

Wettable Powder

| | |
|---|---|
| 2-Chloro-N—[(4,6-dimethoxypyrimidin-2-yl)-aminocarbonyl]-1-naphthalene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

Oil Suspension

| | |
|---|---|
| 2-Chloro-N—[(4,6-dimethylpyrimidin-2-yl)-aminocarbonyl]-1-naphthalene-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 21

Dust

| | |
|---|---|
| 2-Chloro-N—[(4-methoxy-6-methylpyrimidin-2-yl)aminocarbonyl]-1-naphthalene-sulfonamide | 10% |
| attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

Utility

The compounds of the present invention are active herbicides. They have utility for broadspectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application, compounds of this invention may be used to modify plant growth beneficially, and also selectively control weeds in crops such as rice and wheat.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); $\alpha,\alpha,\alpha$-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl(methoxymethyl)acetanilide (alachlor); and 1,1-dimethyl-3-($\alpha,\alpha,\alpha$-trifluoro-m-tolyl)urea (fluometuron).

The activity of these compounds was discovered in greenhouse tests. The tests are described and the data resulting from them are shown below.

0=no effect
10=maximum effect
C=chlorosis or necrosis
D=defoliation
E=emergence inhibition
G=growth retardation
H=formative effects
6Y=abscised bud or flowers Test Procedure A Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a nonphytotoxic solvent solution of the compounds of Table A. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds of Table A. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment. The data in Table A shows that the compounds of this invention are very effective as herbicides and often cause little or no injury to crops such as wheat and rice.

TABLE A

| Structure | kg/ha | BUSH-BEAN | COTTON | MORN-ING-GLORY | COCK-LE-BUR | CASSIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure 1: 4,6-diCH3 pyrimidine sulfonylurea with 2-Cl naphthyl] | 0.4 | 2C,8G | 2C,2H,5G | 1C | 2C,9G | 2C,8G | 1C,5G | 0 | 0 | 0 | 0 | 1C | 2C,9G | 1C | 2C,9H |
| ![structure 2: 4,6-diOCH3 pyrimidine] | 0.4 | 6Y,5C, 8G | 6C,9G | 9C | 10C | 9C | 5C,9G | 2C | 3C,9H | 1C | 0 | 1C,5H | 5C,9G | 0 | 2G |
| ![structure 3: 4,6-diOCH3 triazine] | 0.4 | 6Y,9D, 9G | 7C,9G | 9C | 9C | 5C,9G | 2C,9G | 0 | 2C,3H | 1C,3G | 1C | 2C,5G | 9C | 2C,9G | 2C,9G |
| ![structure 4: OCH3, CH3 triazine] | 0.4 | 6Y,9D, 9G | 6C,9G | 9C | 10C | 9C | 9C | 2C,5G | 2C,5H | 1C,6G | 2C | 7H | 9C | 1C,3G | 2C,9G |

TABLE A-continued

| Structure | kg/ha | MORNING GLORY | COCKLEBUR | CASSIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|
| Structure 1: chlorodecalin-SO$_2$-NH-C(O)-NH-[pyrimidine with CH$_3$, CH$_3$] | 0.4 | 6Y,3C,9G | 3C,9G | 2C,3G | 0 | 3G | 0 | 0 | 0 | 2C,2H,9G | | 1C,3G | 5G |
| Structure 2: chlorodecalin-SO$_2$-NH-C(O)-NH-[pyrimidine with CH$_3$, OCH$_3$] | 0.4 | 6Y,5C,8G | 5C,9G | 6C,9G | 1C,8G | 1C | 2C,7H | 0 | 0 | 2C,9H | 2C,9H | 1C | 2C,9H |

PRE-EMERGENCE

| Structure | kg/ha | MORNING GLORY | COCKLEBUR | CASSIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|
| Structure 3: chlorodecalin-SO$_2$-NH-C(O)-NH-[pyrimidine with CH$_3$, CH$_3$] | 0.4 | 9G | 9H | 1C,8G | 10E | 2C,5G | 2C,9H | 3C | 1C | 1C,8G | 8H | 6G | 8H |
| Structure 4: chlorodecalin-SO$_2$-NH-C(O)-NH-[pyrimidine with OCH$_3$, OCH$_3$] | 0.4 | | | | | | | | | | | | 8H |

TABLE A-continued

| Structure | | | | | | | | | | | | | |
|---|---|---|---|---|---|---|---|---|---|---|---|---|---|
| naphthalene-Cl-SO₂-NH-C(=O)-NH- triazine(OCH₃, OCH₃) | 0.4 | 9C | 9G,9H | 1C | 10E | 3G | 2C,6H | 1C,7G | 1C,7G | 1C,7G | 2C,8H | 3C,9H | 2C,9H |
| naphthalene-Cl-SO₂-NH-C(=O)-NH- triazine(OCH₃, CH₃) | 0.4 | 9G | 9H | 2C,9G | 9G | 3C,7G | 3C,8G | 8G | 6G | 1C,9G | 2C,9H | 2C,9H | 4C,9H |
| naphthalene-Cl-SO₂-NH-C(=O)-NH- triazine(CH₃, CH₃) | 0.4 | 5G | 9H | 5G | 0 | 0 | 0 | 0 | 0 | 2G | 2C | 2C | 0 |
| naphthalene-Cl-SO₂-NH-C(=O)-NH- pyrimidine(CH₃, OCH₃) | 0.4 | 8G | 9H | 9G | 10E | 2C | 3C,9H | 2C,8G | 1C,2G | 9H | 2C,8H | 2C,6H | 2C,9H |

What is claimed is:

1. A composition suitable for controlling the growth of undesired vegetation which comprises an effective amount of a compound of the formula:

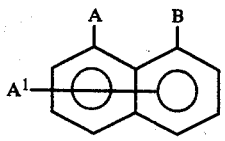

wherein
A¹ is H, F, Cl, Br, CH₃O or NO₂;
A is Cl, F, Br, NO₂, —CH₃, —SO₂NR¹R², —SO₂N(CH₃)(OCH₃), —S(O)$_n$R³, —OR³, —O-SO₂R³ or —OSO₂CF₃;
B is

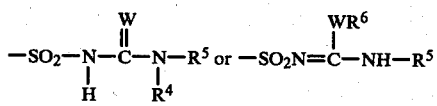

n is 0, 1 or 2;
R¹ is C₁-C₄ alkyl;
R² is C₁-C₄ alkyl;
R³ is C₁-C₄ alkyl;
R⁴ is H or CH₃;

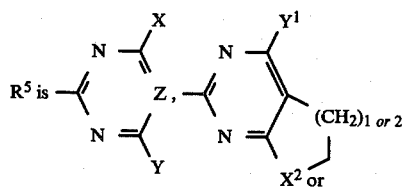

R⁶ is C₁-C₆ alkyl;
R¹⁰ is H or CH₃;
R¹¹ is C₁-C₃ alkyl;
W is O or S;
X is CH₃, CH₃O or CH₃CH₂O;
X² is O or CH₂;
Y is H, C₁-C₃ alkyl, CH₃OCH₂, CH₃CH₂OCH₂, OCH₂CO₂—(H or C₁-C₂ alkyl), OCH(CH₃)CO₂(H or C₁-C₂ alkyl), O—(C₁-C₃ alkyl), O—(C₃-C₄ alkenyl) or NR¹⁰R¹¹;
Y¹ is H, CH₃ or OCH₃;
Y² is H or CH₃; and
Z is CH or CCH₃;
and their agriculturally suitable salts, and at least one of the following: surfactant, solid or liquid diluent.

2. A composition suitable for controlling the growth of undesired vegetation which comprises an effective amount of a compound of the formula:

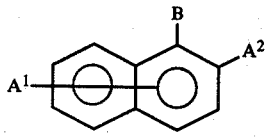

wherein
A¹ is H, F, Cl, Br, CH₃O or NO₂;
A₂ is

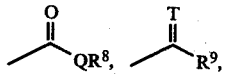

Cl, F, Br, NO₂, —CH₃, —SO₂NR¹R², —SO₂N(CH₃)(OCH₃), —S(O)$_n$R³, —OR³, —OSO₂R³ or —OSO₂CF₃;
B is

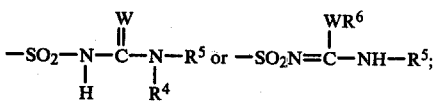

n is 0, 1 or 2;
Q is O, S or NR⁷;
R¹ is C₁-C₄ alkyl;
R² is C₁-C₄ alkyl;
R³ is C₁-C₄ alkyl;
R⁴ is H or CH₃;

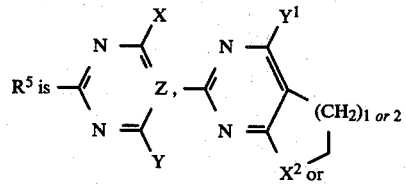

R⁶ is C₁-C₆ alkyl;
R⁷ is H, —OCH₃ or C₁-C₄ alkyl; when Q is O or S then R⁸ is C₁-C₆ alkyl; C₃-C₆ alkenyl, CH₂CH₂OCH₃, CH₂CH₂OCH₂CH₃, C₅-C₆ cycloalkyl, C₄-C₇ cycloalkylalkyl, phenyl, benzyl, or phenyl or benzyl substituted with one or two groups selected from CH₃, Cl or OCH₃; and when Q is O, R⁸ may also be CH₂CH₂Cl; when Q is NR⁷ then R⁸ is H, C₁-C₄ alkyl, C₃-C₄ alkenyl and R⁸ and R⁷ taken together can be —(CH₂)₄—, —(CH₂)₅— or —CH₂CH₂OCH₂CH₂— with the proviso that when R⁷ is CH₃O, R⁸ is CH₃;
R⁹ is C₁-C₆ alkyl, C₃-C₆ alkenyl, C₅-C₆ cycloalkyl, C₄-C₇ cycloalkylalkyl, benzyl, benzyl substituted with one or two groups selected from CH₃, Cl or OCH₃;
R¹⁰ is H or CH₃;
R¹¹ is C₁-C₃ alkyl;
R¹² is C₁-C₃ alkyl or C₃-C₆ alkenyl;

T is O or N—OR$^{12}$;

W is O or S;

X is CH$_3$, CH$_3$O or CH$_3$CH$_2$O;

X$^2$ is O or CH$_2$;

Y is H, C$_1$-C$_3$ alkyl, CH$_3$OCH$_2$, CH$_3$CH$_2$OCH$_2$, OCH$_2$CO$_2$—(H or C$_1$-C$_2$ alkyl), OCH(CH$_3$)CO$_2$(H or C$_1$-C$_2$ alkyl), O—(C$_1$-C$_3$ alkyl), O—(C$_3$-C$_4$ alkenyl) or NR$^{10}$R$^{11}$;

Y$^1$ is H, CH$_3$ or OCH$_3$;

Y$^2$ is H or CH$_3$; and

Z is CH or CCH$_3$;

and their agriculturally suitable salts, and at least one of the following: surfactant, solid or liquid diluent.

3. A composition of claim 1 where

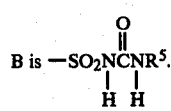

4. A composition of claim 2 where

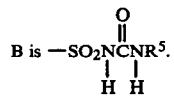

5. A composition of claim 3 where A is Cl, NO$_2$, CH$_3$, OCH$_3$, CH$_3$SO$_2$O, CH$_3$SO$_2$, SO$_2$N(CH$_3$)$_2$, SO$_2$N(CH$_3$)(OCH$_3$), CH$_3$S or CH$_3$SO.

6. A composition of claim 5 where A$^1$ is H.

7. A composition of claim 6 where Y is CH$_3$ or CH$_3$O, X$^2$ is O and Y$^2$ is CH$_3$.

8. A composition of claim 7 where A is Cl.

9. A composition of claim 4 where A$^2$ is Cl, NO$_2$, CH$_3$, CH$_3$O, CH$_3$SO$_2$O, CH$_3$SO$_2$, SO$_2$N(CH$_3$)$_2$, SO$_2$N(CH$_3$)(COH$_3$), CH$_3$S or CH$_3$SO.

10. A composition of claim 9 where A$^1$ is H.

11. A composition of claim 10 where X$^2$ is O, Y is CH$_3$ or CH$_3$O and Y$^2$ is CH$_3$.

12. A composition of claim 11 where A$^2$ is Cl.

13. The composition of claim 12 where the compound is 2-chloro-N-[(4,6-dimethoxypyrimidine-2-yl)aminocarbonyl]-1-naphthalenesulfonamide.

14. A method for controlling the growth of undesired vegetation which comprises applying to the locus to be protected an effective amount of a composition of any of claims 1–13.

* * * * *